US007034110B2

(12) United States Patent
Hogan, Jr.

(10) Patent No.: US 7,034,110 B2
(45) Date of Patent: Apr. 25, 2006

(54) METHOD OF IDENTIFYING CHEMICAL COMPOUNDS HAVING SELECTED PROPERTIES FOR A PARTICULAR APPLICATION

(75) Inventor: Joseph C. Hogan, Jr., Belmont, MA (US)

(73) Assignee: ArQule, Inc., Woburn, MA (US)

( * ) Notice: Subject to any disclaimer, the term of this patent is extended or adjusted under 35 U.S.C. 154(b) by 11 days.

(21) Appl. No.: 10/764,112

(22) Filed: Jan. 23, 2004

(65) Prior Publication Data

US 2004/0161610 A1  Aug. 19, 2004

Related U.S. Application Data

(63) Continuation of application No. 08/177,497, filed on Jan. 5, 1994, now abandoned.

(51) Int. Cl.
*C07K 7/04* (2006.01)
*C07D 223/12* (2006.01)
*C07D 413/12* (2006.01)
*C07D 265/28* (2006.01)

(52) U.S. Cl. ............... 530/330; 530/331; 540/606; 544/146; 544/153; 544/156; 544/162; 544/164; 544/379; 544/382; 544/402; 546/212; 546/214; 548/228; 564/153; 564/155; 564/197

(58) Field of Classification Search .......... 530/330, 530/331; 540/606; 544/146, 153, 156, 162, 544/164, 379, 382, 402; 546/212, 214; 548/228; 564/153, 155, 197
See application file for complete search history.

(56) References Cited

U.S. PATENT DOCUMENTS

| 3,410,880 A | 11/1968 | Brockenhurst |
| 3,450,673 A | 6/1969 | McKillip |
| 3,485,806 A | 12/1969 | Bloomquist et al. |
| 3,488,327 A | 1/1970 | Kollinsky et al. |
| 3,488,389 A | 1/1970 | McKillip |
| 3,499,032 A | 3/1970 | Clemens et al. |
| 3,511,894 A | 5/1970 | Markert |
| 3,527,802 A | 9/1970 | Slagel |
| 3,555,095 A | 1/1971 | Slagel |
| 3,565,868 A | 2/1971 | Sedor et al. |
| 3,567,725 A | 3/1971 | Grabowski et al. |
| 3,583,950 A | 6/1971 | Kollinsky et al. |
| 3,598,790 A | 8/1971 | Kollinsky et al. |
| 3,641,145 A | 2/1972 | Culbertson |
| 3,664,990 A | 5/1972 | Slagel |
| 3,671,473 A | 6/1972 | Sedor et al. |
| 3,676,453 A | 7/1972 | Pines et al. |
| 3,704,128 A | 11/1972 | Koda et al. |
| 3,706,797 A | 12/1972 | McKillip et al. |
| 3,706,800 A | 12/1972 | Hartlage et al. |
| 3,715,343 A | 2/1973 | Slagel et al. |
| 3,728,387 A | 4/1973 | Freis et al. |
| 3,756,994 A | 9/1973 | Culbertson |
| 3,781,319 A | 12/1973 | Wawzonek et al. |
| 3,794,495 A | 2/1974 | Ishihara et al. |
| 3,803,220 A | 4/1974 | Gasman |
| 3,811,887 A | 5/1974 | Ishihara et al. |
| 3,818,065 A | 6/1974 | Schoellkopf et al. |
| 3,850,969 A | 11/1974 | Grimm et al. |
| 3,893,974 A | 7/1975 | Niino et al. |
| 3,898,087 A | 8/1975 | Brutchen et al. |
| 3,904,749 A | 9/1975 | McKillip |
| 3,925,284 A | 12/1975 | Carleton et al. |
| 3,934,029 A | 1/1976 | Kabara |
| 3,934,031 A | 1/1976 | Kabara |
| 3,934,035 A | 1/1976 | Kabara |
| 3,946,131 A | 3/1976 | Biefeld et al. |
| 3,948,866 A | 4/1976 | Pennewiss et al. |
| 3,968,065 A | 7/1976 | Morris et al. |
| 3,969,298 A | 7/1976 | Gasman |
| 3,985,807 A | 10/1976 | Grimm et al. |
| 4,005,055 A | 1/1977 | Miron et al. |

(Continued)

FOREIGN PATENT DOCUMENTS

EP  0 185 493  6/1986

(Continued)

OTHER PUBLICATIONS

U.S. Appl. No. 08/092,862, filed Jul. 1993, Armstrong.

(Continued)

*Primary Examiner*—Peter O'Sullivan
(74) *Attorney, Agent, or Firm*—Arnold & Porter LLP

(57) ABSTRACT

A method for obtaining compounds having selected properties for a particular application by forming base modules having at least two structural diversity elements from the reaction of a first compound having at least one structural diversity element and a first reactive group, with a second compound having at least one structural diversity element and a second reactive group, wherein the first and second groups combine by an addition reaction; producing a first array of molecules by varying at least one of the structural diversity elements of the compounds when producing the base modules; and screening the array to determine a first suitable compound for the particular application. The base modules are preferably formed form oxazolone- and aminimide-derived compounds. If desired, the method can be repeated by producing a second array of molecules through the formation of base modules having structural diversity elements that are modified from those of the first suitable compound; and screening the second array of molecules to determine a second suitable compound for the particular application. The second array producing and screening steps can be repeated as often as necessary to achieve an optimum compound for the particular application.

13 Claims, 1 Drawing Sheet

U.S. PATENT DOCUMENTS

Figure 1:
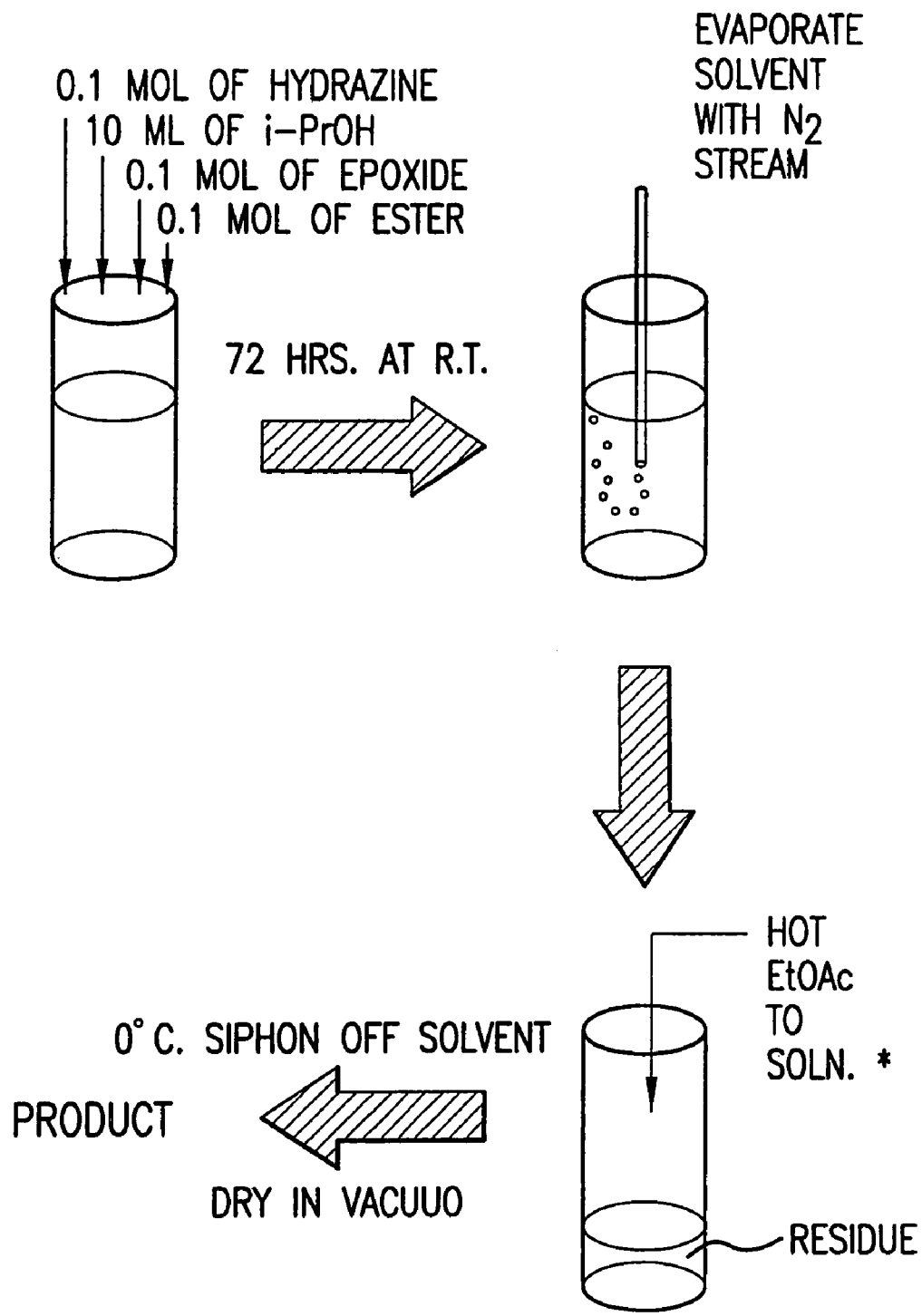

| | | |
|---|---|---|
| 4,016,340 A | 4/1977 | Kolesinski et al. |
| 4,022,623 A | 5/1977 | Fitzgerald et al. |
| 4,046,658 A | 9/1977 | Brown |
| 4,067,830 A | 1/1978 | Kresta |
| 4,070,348 A | 1/1978 | Kraemer et al. |
| 4,078,901 A | 3/1978 | Sung et al. |
| 4,080,206 A | 3/1978 | Kolesinski et al. |
| 4,097,444 A | 6/1978 | Teige et al. |
| 4,102,916 A | 7/1978 | Falk |
| 4,122,159 A | 10/1978 | Madrange et al. |
| 4,140,680 A | 2/1979 | Sullivan |
| 4,162,355 A | 7/1979 | Tsibris |
| 4,189,481 A | 2/1980 | Kabara |
| 4,212,905 A | 7/1980 | Tsibris |
| 4,213,860 A | 7/1980 | Tsibris |
| 4,217,364 A | 8/1980 | Kabara |
| 4,260,705 A | 4/1981 | Tsibris |
| 4,280,008 A | 7/1981 | Schoellkopf et al. |
| 4,304,705 A | 12/1981 | Heilmann et al. |
| 4,378,411 A | 3/1983 | Heilmann et al. |
| 4,424,272 A | 1/1984 | Taylor |
| 4,451,619 A | 5/1984 | Heilmann et al. |
| 4,485,236 A | 11/1984 | Rasmussen et al. |
| 4,548,981 A | 10/1985 | Kolesinski et al. |
| 4,617,253 A | 10/1986 | Taylor et al. |
| 4,624,995 A | 11/1986 | Katritzky et al. |
| 4,631,211 A | 12/1986 | Houghten |
| 4,667,012 A | 5/1987 | Rasmussen et al. |
| 4,670,528 A | 6/1987 | Taylor et al. |
| 4,695,608 A | 9/1987 | Engler et al. |
| 4,705,824 A | 11/1987 | Lin |
| 4,737,560 A | 4/1988 | Heilmann et al. |
| 4,740,568 A | 4/1988 | Katritzky et al. |
| 4,777,217 A | 10/1988 | Rasmussen et al. |
| 4,777,276 A | 10/1988 | Rasmussen et al. |
| 4,785,070 A | 11/1988 | Rasmussen et al. |
| 4,816,554 A | 3/1989 | Katritzksy et al. |
| 4,841,021 A | 6/1989 | Katritzy et al. |
| 4,852,969 A | 8/1989 | Babirad et al. |
| 4,871,824 A | 10/1989 | Heilmann et al. |
| 4,874,822 A | 10/1989 | Rasmussen et al. |
| 4,898,923 A | 2/1990 | Katritzky et al. |
| 4,948,715 A | 8/1990 | Hulme-Lowe et al. |
| 4,981,933 A | 1/1991 | Fazio et al. |
| 5,010,175 A | 4/1991 | Rutter et al. |
| 5,013,795 A | 5/1991 | Coleman et al. |
| 5,039,813 A | 8/1991 | Fazio et al. |
| 5,053,454 A | 10/1991 | Judd |
| 5,066,559 A | 11/1991 | Elmasry et al. |
| 5,075,352 A | 12/1991 | Elmasry |
| 5,081,197 A | 1/1992 | Heilmann et al. |
| 5,091,489 A | 2/1992 | Heilmann et al. |
| 5,094,766 A | 3/1992 | Kapuscinski et al. |
| 5,138,071 A | 8/1992 | Schoellkopf et al. |
| 5,143,854 A | 9/1992 | Pirrung et al. |
| 5,147,957 A | 9/1992 | Kumar |
| 5,149,806 A | 9/1992 | Moren et al. |
| 5,157,108 A | 10/1992 | Krepski et al. |
| 5,157,145 A | 10/1992 | Schoellkopf et al. |
| 5,175,081 A | 12/1992 | Krepski et al. |
| 5,182,366 A | 1/1993 | Huebner et al. |
| 5,185,102 A | 2/1993 | Harelstad et al. |
| 5,194,623 A | 3/1993 | Krepski et al. |
| 5,200,471 A | 4/1993 | Coleman et al. |
| 5,223,409 A | 6/1993 | Ladner et al. |
| 5,225,533 A | 7/1993 | Rutter et al. |
| 5,288,514 A | 2/1994 | Ellman |
| 5,300,425 A | 4/1994 | Kauvar |
| 5,324,483 A | 6/1994 | Cody et al. |
| 5,359,115 A | 10/1994 | Campbell et al. |
| 5,367,053 A | 11/1994 | Dooley et al. |
| 5,424,186 A | 6/1995 | Fodor et al. |
| 5,449,754 A | 9/1995 | Nishioka |
| 5,463,564 A | 10/1995 | Agrafiotis et al. |
| 5,464,759 A | 11/1995 | Coolidge et al. |
| 5,503,805 A | 4/1996 | Sugarman et al. |
| 5,525,734 A | 6/1996 | Gallop et al. |
| 5,525,735 A | 6/1996 | Gallop et al. |
| 5,545,568 A | 8/1996 | Ellman |
| 5,571,698 A | 11/1996 | Ladner et al. |
| 5,574,656 A | 11/1996 | Agrafiotis et al. |
| 5,609,826 A | 3/1997 | Cargill et al. |
| 5,614,608 A | 3/1997 | Krchnak et al. |
| 5,639,866 A | 6/1997 | Kahne |
| 5,646,285 A | 7/1997 | Baindur et al. |
| 5,651,943 A | 7/1997 | Lam et al. |
| 5,663,046 A | 9/1997 | Baldwin et al. |
| 5,670,326 A | 9/1997 | Beutel |
| 5,684,711 A | 11/1997 | Agrafiotis et al. |
| 5,738,996 A | 4/1998 | Hodges et al. |
| 5,744,305 A | 4/1998 | Fodor et al. |
| 5,766,556 A | 6/1998 | DeWitt et al. |
| 5,770,455 A | 6/1998 | Cargill et al. |
| 5,792,431 A | 8/1998 | Moore et al. |
| 5,807,683 A | 9/1998 | Brenner |
| 5,831,014 A | 11/1998 | Cook et al. |
| 5,846,841 A | 12/1998 | Sepetov et al. |
| 5,864,010 A | 1/1999 | Cook et al. |
| 5,877,278 A | 3/1999 | Zuckermann et al. |
| 5,958,702 A | 9/1999 | Benner |
| 5,968,736 A | 10/1999 | Still et al. |
| 5,985,356 A | 11/1999 | Schultz et al. |
| 5,985,551 A | 11/1999 | Brennan |
| 6,001,579 A | 12/1999 | Still et al. |
| 6,060,596 A | 5/2000 | Lerner et al. |
| 6,096,276 A | 8/2000 | Laursen |
| 6,121,048 A | 9/2000 | Zaffaroni et al. |
| 6,245,937 B1 | 6/2001 | Cheng et al. |
| 6,319,668 B1 | 11/2001 | Nova et al. |

FOREIGN PATENT DOCUMENTS

| | | |
|---|---|---|
| EP | 0 212 617 B1 | 1/1989 |
| EP | 0 604 552 B1 | 2/1997 |
| EP | 0 734 530 B1 | 11/1997 |
| EP | 0 643 778 B1 | 5/2000 |
| GB | 1 181 218 | 2/1970 |
| GB | 1 265 163 | 3/1972 |
| JP | 63 17933 | 4/1988 |
| WO | 90/15070 | 12/1990 |
| WO | 91/17271 | 11/1991 |
| WO | 91/19735 | 12/1991 |
| WO | 91/19818 | 12/1991 |
| WO | 92/10092 | 6/1992 |
| WO | 93/09668 | 5/1993 |
| WO | 93/20242 | 10/1993 |
| WO | 93/22684 | 11/1993 |
| WO | 94/08051 | 4/1994 |
| WO | 94/08711 | 4/1994 |
| WO | 95/02566 | 1/1995 |
| WO | 95/16209 | 6/1995 |
| WO | 95/32425 | 11/1995 |
| WO | 95/35278 | 12/1995 |
| WO | 96/23749 | 8/1996 |

OTHER PUBLICATIONS

Armstrong, Robert W. et al., "Analogs of the Azinomycins: Selective Acetylation via Orthoacetate Hydrolysis," (Abstract), (1993).

Baldwin et al., "Synthesis of a Small Molecule Combinatorial Library Encoded with Molecular Tags," *J. Am. Chem. Soc.*, 117:5588-5589, (1995).

Barbas et al., "Direct selection of antibodies that coordinate metals from semisynthetic combinatorial libraries," *Proc. Natl. Acad. Sci. U.S.A.*, 90:6385-6389 (1993).

Boyce et al., 1994, "Peptidosteroidal Receptors for Opioid Peptides. Sequence-Selective Binding Using a Synthetic Receptor Library," *J. Am. Chem. Soc.*, 116:7955-7956.

Bray, Andrew M. et al., "The Simultaneous Multiple Production of Solution Phase Peptides: Assessment of the Geysen Method of Simultaneous Peptide Synthesis," *Tetrahedron Letters*, vol. 31, No. 40, pp. 5811-5814, 1990.

Brenner and Lerner, 1992, "Encoded combinatorial chemistry," *Proc. Natl. Acad. Sci. U.S.A.*, 89:5381-5383.

Bunin and Ellman, 1992, "A General and Expedient Method for the Solid-Phase Synthesis of 1,4-Benzodiazepine Derivatives," *J. Am. Chem. Soc.*, 114:10997-10998.

Bunin et al., 1994, "The combinatorial synthesis and chemical and biological evaluation of a 1,4-benzodiazepine library," *Proc. Natl. Acad. Sci. U.S.A.*, 91:4708-4712.

Burbaum et al., 1995, "A paradigm for drug discovery employing encoded combinatorial libraries," *Proc. Natl. Acad. Sci. U.S.A.*, 92:6027-6031.

Campbell et al., 1995, "A Transition State Analogue Inhibitor Cominatorial Library," *J. Am.Chem. Soc.* 117:5381-5382.

Carell et al., 1995, "New promise in combinatorial chemistry: synthesis, characterization, and screening of small-molecule libraries in solution," *Chemistry and Biology* 2:171-183.

Chabala, 1995, "Solid-phase combinatorial chemistry and novel tagging methods for identifying leads," *Current Opinion in Biotechnology* 6:632-639.

Chen et al., 1994, "Analogous Organic Synthesis of Small-Compound Libraries: Validation of Combinatorial Chemistry in Small Molecule Synthesis," *J. Am. Chem. Soc.* 116:2661-2662.

Cho et al., 1993, "An Unnatural Biopolymer," *Science* 261:1303-1305.

Christian et al., 1992, "Simplified Methods for Construction, Assessment and Rapid Screeing of Peptide Libraries in Bacteriophage," *J. Mol. Biol.*, 227:711-718.

Combs, Andrew Paul, 1994, "Syntheses and Structure-Activity Relationship Analyses of Dehydroamino Acid Derivatives Related to the Azinomycins," Dissertation, University of California (Thesis and Abstract of Thesis).

Combs, Andrew Paul et. al., 1993, "Highly Convergent Synthesis of Azinomycin Analogs Via Passerini Reactions of Vinylaziridine Isocyanides," *Am. Chem. Soc.* vol. 206(1-2): 367.

Cwirla et al., 1990, "Peptides on phage: A vast library of peptides for identifying ligands," *Proc. Natl. Acad. Sci. U.S.A.* 87:6378-6382.

Desai et al., 1994, "Recent Advances in the Generation of Chemical Diversity of Libraries," *Drug Development Research* 33:174-188.

Devlin et al., 1990, "Random Peptide Libraries: A Source of Specific Protein Binding Molecules," *Science* 249:404-406.

DeWitt et al., "Diversomers: An aproach to non-peptide, nonoligomeric chemical diversity," *Proc. Natl. Acad. Sci. U.S.A.* 90:6909-6913 (1993).

Ecker et al., 1993, "Rational screening of oligonucleotide combinatorial libraries for drug discovery," *Nucleic Acids Res.* 21:1853-1856.

Eichler et al., "Cyclic Peptide Template Combinatorial Libraries: Synthesis and Identification of Chymotrypsin Inhibitors," *Peptide Research* 7:300-307 (1994).

Ellman, 1996, "Design, Synthesis and Evaluation of Small-Molecule Libraries," *Acc. Chem. Res.* 29:132-143.

Erb et al., 1994, "Recursive deconvolution of combinatorial chemical libraries," *Proc. Natl. Acad. Sci. U.S.A.* 91:11422-11426.

Fodor et al., 1991, "Light-Directed, Spatially Addressable Parallel Chemical Synthesis," *Science* 251:767-773.

Freier et al., 1995, "Deconvolution of Combinatorial Libraries for Drug Discovery: A Model System," *J. Med. Chem.* 38:344-352.

Furka et al., 1991, "General method for rapid synthesis of multicomponent peptide mixtures," *Int. J. Peptide Protein Res.* 37:487-493.

Gallop et al., 1994, "Applications of Combinatorial Technologies to Drug Discovery. 1. Background and Peptide Combinatorial Libraries," *J. Med. Chem.* 37:1233-1251.

Garr et al., "Current Technology Applied to Established Chemical Knowledge: A Novel Approach to Small Molecule Chemical Libraries" Chem. Div., Panlabs, Inc. (Abstract), (1993).

Geysen and Mason, 1993, "Screening chemically synthesized peptide libraries for biologically-relevant moleucles," *Bioorganic & Medicinal Chemistry Letters* 3: 397-404.

Geysen et al., 1987, "Strategies for epitope analysis using peptide synthesis," *Journal of Immunological Methods* 102: 259-274.

Gordon et al., "Applications of Cominatorial Technologies to Drug Discovery. 2. Combinatorial Organic Synthesis, Libarary Screening Strategies, and Future Directions," *J. Med. Chem.* 37:1386-1401 (1994).

Han et al., 1995, "Liquid-phase combinatorial synthesis," *Proc. Natl. Acad. Sci. U.S.A.* 92:6419-6423.

Houghten, 1985, "General method for the rapid solid-phase synthesis of large numbers of peptides: Specificity of antigen-antibody interaction at the level of individual amino acids," *Proc. Natl. Acad. Sci U.S.A.* 82:5131-5135.

Houghten et al., 1991, "Generation and use of synthetic peptide combinatorial libraries for basic research and drug discovery," *Nature* 354:84-86.

Houghten, Richard A., "The broad utility of soluble peptide libraries for drug discovery," *Gene*, 137:7-11 (1993).

Jacobs and Fodor, 1994, "Combinatorial chemistry—applications of light-directed chemical synthesis," *TIBTECH* 12:19-26.

Jung and Beck-Sickinger, 1992, "Multiple Peptide Synthesis Methods and Their Applications," *Angew. Chem. Int. Ed. Engl.*, 31:367-383.

Kerr et al., 1993, "Encoded Combinatorial Peptide Libraries Containing Non-Natural Amino Acids," *J. Am. Chem. Soc.* 115:2529-2531.

Kick and Ellman, 1995, "Expedient Method for the Solid-Phase Synthesis of Aspartic Acid Protease Inhibitors Directed Toward the Generation of Libraries," *J. Med. Chem.* 38:1424-1430.

Krchňák and Lebl, 1995, "Synthetic library techniques: Subjective (biased and generic) thoughts and views," *Molecular Diversity* 1:193-216.

Lam et al., 1991, "A new type of synthetic peptide library for identifying ligand-binding activity," *Nature* 354:82-84.

Latham et al., 1994, "The application of a modified nucleotide in aptamer selection: novel thrombin aptamers containing 5-(1-pentynyl)2'-deoxyuriine," *Nucleic Acids Res.* 22:2817-2822.

Martin et al., 1995, "Measuring Diversity: Experimental Design of Combinatorial Libraries for Drug Discovery," *J. Med. Chem.* 38:1431-1436.

Moran et al., 1995, "Radio Frequency Tag Encoded Combinatorial Library Method for the Discovery of Tripeptide-Substituted Cinnamic Acid Inhibitors of the Protein Tyrosine Phosphatase PTP1B," *J. Am. Chem. Soc.* 117:10787-10788.

Murphy et al., 1995, "Combinatorial Organic Synthesis of Highly Functionalized Pyrrolidines: Identification of a Potent Angiotensin Converting Enzyme Inhibitor from a Mercaptoacyl Proline Library," *J. Am. Chem. Soc.* 117:7029-7030.

Needels et al., 1993, "Generation and screening of an oligonucleotide-encoded sythetic peptide library," *Proc. Natl. Acad. Sci. U.S.A.* 90:10700-10704.

Nielsen et al., 1993, "Synthetic Methods for the Implementation of Encoded Combinatorial Chemistry," *J. Am. Chem. Soc.* 115:9812-9813.

Nikolaiev et al., 1993, "Peptide-Encoding for Structure Determination of Nonsequenceable Polymers within Libraries Synthesized and Tested on Solid-Phase Supports," *Peptide Research* 6(3):161-170.

Ohlmeyer et al., 1993, "Complex synthetic chemical libraries indexed with molecular tags," *Proc. Natl. Acad. Sci. U.S.A.* 90:10922-10926.

Ostresh et al., 1994, "Libraries from libraries: Chemical transformation of combinatorial libraries to extend the range and repertoire of chemical diversity," *Proc. Natl. Acad. Sci. U.S.A.* 91:11138-11142.

Pavia, Michael R. et al., "The Generation of Molecular Diversity," *Bioorganic & Medicinal Chemistry Letters*, vol. 3(3):387-396 (1993).

Pease et al., 1994, "Light-generated oligonucleotide arrays for rapid DNA sequence analysis," *Proc. Natl. Acad. Sci. U.S.A.* 91:5022-5026.

Pinilla et al., "Investigation of antigen-antibody interactions using a coluble, non-support-bound synthetic decapeptide library composed of four trillion ($4 \times 10^{12}$) sequences," *Biochem. J.* 301:847-853 (1994).

Posner et al., 1994, "Catalytic antibodies: perusing combinatorial libraries," *TIBS* 19:145-150.

Romanovskis et. al., "Cyclic Peptide Libraries: Recent Developments" Dept. of Chem., U. of Louisville (Abstract), (1993).

Scott, 1992, "Discovering peptide ligands using epitope libraries," *TIBS* 17:241-245.

Scott and Smith, 1990, "Searching for Peptide Ligands with an Epitope Library," *Science* 249:386-390.

Sepetov et al., 1995, "Library of libraries: Approach to synthetic combinatorial library design and screening of 'pharmacophore' motifs," *Proc. Natl. Acad. Sci. U.S.A.* 92:5426-5430.

Simon et al., 1992, "Peptoids: A modular approach to drug discovery," *Proc. Natl. Acad. Sci. U.S.A.* 89:9367-9371.

Staňková et al., 1994, "Application of One-Bead One-Structure Approach to Identification of Nonpeptide Ligands," *Drug Development Research* 33:146-156.

Stephen and Lane, 1992, "Mutant Conformation of p53: Precise Epitope Mapping Using a Filamentous Phage Epitope Library.".

Wallace et al., 1994, "A Multimeric Synthetic Peptide Combinatorial Library," *Peptide Research* 7:27-31.

Wu et al., 1994, "Identifying Substrate Motifs of Protein Kinases by a Random Library Approach," *Biochemistry* 33:14825-14833.

Zuckermann et al., 1994, "Discovery of Nanomolar Ligands for 7-Transmembrane G-Protein-Coupled Receptors from a Diverse N-(Substituted)glycine Peptoid Library," *J. Med. Chem.* 37:2678-2685.

Zuckerman, Ronald N., 1993, "The chemical synthesis of peptidomimetic libraries," *Current Opinion in Structure Biology*, 3:580-584.

Aubry et al., "Experimental Conformational Study of Two Peptides Containing a-Aminoisobutyric Acid. Crystal Structure of N-Acetyl-a-aminoisobutyric Acid Methylamide", *Biopolymers*, 17:1693-1711 (1978).

Barker, C. C., "The Dehydration and Racemisation of N-Acyl-L-aspartic Acids by Acetic Anhydride", University College, Hull, pp. 453-456 (1952).

Benedetti, Ettore, "Solid-State and Solution Conformation of Homo Oligo-($\alpha$-aminoisobutyric acids) from Tripeptide to Pentapeptide: Evidence for a $3 1_{10}$ Helix[1a]", *J. Am. Chem. Soc.*, 104:2437-2444 (1982).

Benedetti et al., Folded and Extended Structures of Homooligopeptides from $\alpha,\alpha$-Dialkylated Glycines. A Conformational Energy Computation and X-ray Diffraction Study, *J. Am. Chem. Soc.* 106:8146-8152 (1984).

Benedetti et al., "First Crystal Structure Analysis of a Complete Homo-Oligopeptide Series", *Instituto Chimico, University of Naples, Italy*, pp. 619-624, (1980).

Bonora, Gian Maria, "Folded and Extended Structures of Homooligopeptides from $\alpha,\alpha$-Dialkylated $\alpha$-Amino Acids. An Infrared Absorption and H Nuclear Magnetic Resonance Study", *J. Am. Chem. Soc.*, 106:8152-8156 (1984).

Bonora et al., "Synthesis of a Homologous Series of Protected Oligopeptides Derived From L-Norvaline", *Bull. Soc. Chim. Belg.*, 84(4):299-304 (1975).

Bosch et al., "(-)-Isovaline: Confirmation of its D-(+R)-Configuration by X-Ray Analysis of Its N-Chloroacetyl Derivative", *Tetrahedron* 38(24):3579-3583 (1982).

Bosch et al., "Structure of the $3_{10}$-Helical Pentapeptide Boc-Aib-L-Ala-Aib-L-Ala-Aib-OMe Dihydrate, $C_{24}H_{43}N_6O_9 2H_2O$," *Acta Cryst.* C39 pp. 776-778 (1983).

Brown, Melancthon S., "Preparation of Some New Aminimides", *Journal of Chemical and Engineering Data*, 12(4) (1967).

Burgess et al., "An Obligatory a-Helical Amino Acid Residue", *Biopolymers*, 12:2599-2605 (1973).

Cleaver et al., "Synthesis of 2,2'-Bis-[5(4H)-oxazolones]", 77:1544-1546 (1955).

Corkill et al., "Light Scattering by Polydisperse Cylindrical Micelles", *Newcastle Technical Centre*, pp. 1274-1280 (1969).

Culbertson, B.M, "Aminimides. VII Homo- and Copolymerization Studies on 1,1-Dimethyl-1-(2-hydroxypropyl)amine-Methacrylimide and 1,1-Dimethyl-1-1(2,3-dihydroxypropyl)amine-Methacrylimide," *Macromolecules*, vol. 1, p. 254, Jun. 1968.

Culbertson et al., "Synthesis and Polymerization Studies of aminimide Monomers containing Acetoxyl or Carboxylic Acid Residues", *Applied Polymer Symposium*, 26:339-410 (1975).

Dharanipragada et al., "Asymmetric Synthesis of Unusual Amino Acids: An Efficient Synthesis of Optically Pure Isomers of β-Methylphenylalanine", *Tetrahedron*, 48(23):4733-4748 (1992).

Fazio et al., "Synthesis and Reactivity of Highly Versatile VDMO-VBC Copolymers", *Polymer Bulletin 22*, pp. 449-454 (1989).

Fox, Jr., et al., "A voltage-gated ion channel model inferred from the crystal structure of alamethicin at 1.5-A resolution", *Nature*, 300:325-330 (1982).

Francis, A.K., "The Crystal Structure of a $3_{10}$ Helical Decapeptide Containing α-Aminoisobutryic Acid", *FEBS Letters*, 155(2):230-232 (1993).

Francis, Athappilly K., "The Crystal Structure of the Amino-Terminal Pentapeptide of Suzukacillin. Occurrence of a Four-fold Peptide Helix", *J. Chem. Soc. Perkin Trans. II*, 1235-1239 (1982).

Francis et al., "Crystal Structure of Boc-Ala-Aib-Ala-Aib-Aib-Methyl Ester, A Pentapeptide Fragment of the Channel-Forming Ionophore Suzukacillin", *Biopolymers*, 22:1499-1505 (1983).

Haas et al., "Thermally Reversible Homopolymer Gel Systems", *Polymer Letters*, 2:1095-1096 (1964).

Hardy et al., "Peptides Containing Dipropyglycine: Part 1. Preparation of protected derivatives of dipropylglycine and their incorporation into dipeptides,", *Int. J. Peptide Protein Res.*, 21:392-405 (1983).

Hardy et al., "Peptides Containing Dipropyglycine: Part 2. Preparation of tripeptides and higher homo-oligomers of dipropylglycine," *Int. J. Peptide Protein Res.*, (1983), pp. 406-418.

Heilmann et al., "The Chemistry of 2-Alkenyl-2-Oxazolin-5-Ones," *Central Research Laboratories, 3M Corp.* (1982).

Heilmann et al., "Chemistry of Alkenyl Azlactones. IV. Preparation and Properties of Telechelic Acrylamides Derived from Amine-terminated Oligomers", *Journal of Polymer Science, Polymer Chemistry Edition*, 22:3149-3160 (1984).

Hinds, Mark G., "Synthesis, Conformational Properties, and Antibody Recognition of Peptides Containing β-Turn Mimetics Based on α-Alkylproline Derivatives", *J. Med. Chem.*, 34:1777-1789 (1991).

Hruby et al., "Conformational and Dynamic Considerations in the Design of Peptide Hormone Analogs", *Biopolymers*, 22:517-530 (1983).

Hubner, Van Klaus et al., "Die Angewandte Makromolekulare Chemie 11," *Synthese und Reaktionen*, pp. 109-124 (1970).

Inubushi et al., "Thermal Decomposition Behavior of Mono-aminimides and Their Application to Polymerization of Epoxide", *Journal of Polymer Science: Part A: Polymer Chemistry*, 25:137-150 (1987).

Inubushi et al., "Tough Epoxy Resins Cured with Aminimides", *Journal of Polymer Science, Part A: Polymer Chemistry*, 26:1779-1789 (1988).

Iwakura et al., "Synthesis of N-[1-(1-Substituted 2-oxopropyl)]acrylamides and -methacrylamides. Isolation and Some Reactions of Intermediates of the Dakin-West Reaction", *The Journal of Organic Chemistry*, (1966).

Jung, G., "Stabilizing Effects of 2-Methylalaline Residues on β-Turns and α-Helixes", *Biopolymers*, 22:241-246 (1983).

Jung, Gunther, "Structure and Activity of Natural Peptides, Properties of the Membrane Modifying Polypeptide Antibiotics Alamethicin and Trichotoxin A-40," Walter deGruyter Berlin, 1981, pp. 76-114.

Kazmierski et al., "Topographic Design of Peptide Neurotransmitters and Hormones on Stable Backbone Templates: Relation of Conformation and Dynamics to Bioactivity", *J. Am. Chem. Soc.*, 113:2275-2283 (1991).

Leibfritz, Dieter, "Syntheses von 2-Methylalanin-Peptiden, die pH-Abhangigkeit Ihrer $^{13}$C-NMR-Spektren und Eine Neue Methode Zur Auswertung uber CS-Diagramme", *Tetrahedron*, 38(14):2165-2181 (1982).

Leplawy, M.T. et al., "Synthesis of Peptides Derived from Alpha-Methylalanine," *Tetrahedron*, vol. 11, pp. 39-51, (1960).

Marshall, Garland R., "Intra-Science Chemistry Reports," vol. 5, No. 4 (1971), pp. 305-316, *Studies on the Biologically-Active Conformations of Angiotensin*.

Marshall et al., "Angiotensin II—Studies on the Biologically Active Conformation", *Supplement II to Circulation Research*, vols. XXX and XXXI:143-150 (1972).

Mayr et al., "Die Kristallstruktur von α-(tert-Butyloxycarbonylamino)-isobuttersaure", *Liebigs Ann. Chem.*, 715-724 (1980).

McKillip et al., "The Chemistry of Aminimides", *Chemical Reviews*, 73(3):255-281 (1973).

Mierke et al., "Peptidomimetics in the Study of Opiate Peptides", *Chemistry Department, University of California, San Diego, Clinical Research Institute of Montreal, Montreal Quebec, Canada H2W 1R7, Structural Biology*, pp. 348-350, (1989).

Muthiah et al., "Copolymers of 2-Vinyl-4,4-Dimethylazlactone with Styrene and Ethyl α-Hydroxymethylacrylate", *Jounral of Polymer Science: Part A: Polymer Chemistry*, 29:29-37 (1991).

Nagaraj et al., "Alamethicin, a Transmembrane Channel", *Acc. Chem. Res.*, 14:356-362 (1981).

Nagaraj et al., "Stereochemically Constrained Linear Peptides. Conformations of Peptides Containing α-Aminoisobutyric Acid", *J. Am. Chem. Soc.*, 101(1):16-20 (1979).

Nair et al., "Structure of a Peptide Oxazolone: 2-(1-Benzyloxycarbonylamino-1'-methylethyl)-4,4-dimethyl-5-oxazolone", *Acta Cryst.*, B36:1498-1500 (1980).

Nicolas, Ernesto, "Asymmetric Synthesis of Unusual Amino Acids: Synthesis of Optically Pure Isomers of β-methyltyrosine", *Tetrahedron Letters*, 30(49):6845-6848 (1989).

Niino et al., "Aminimide as Hardener/Curing Promoter for One Part Epoxy Resin Composition", *J. Applied Polymer Science*, 27:2361-2368 (1982).

Paterson et al., "Sensitivity of Polypeptide Conformation to Geometry. Theoretical Conformational Analysis of Oligomers of α-Aminoisobutyric Acid", *J. Am. Chem. Soc.*, 103(11):2947-2955 (1981).

Peters et al., "Quantum Theory of the Structure and Bonding in Proteins", *J. Molecular Structure*, 86:341-347 (1982).

Prasad et al., "Molecular Structure of Boc-Aib-Aib-Phe-Met-$NH_2$ DMSO. A Fragment of a Biologically Active Enkephalin Analogue", *J. Chem. Soc. Perkin Trans*, 1:417-421 (1983).

Rao et al., "Hydrophobic Channels in Crystals of an α-Aminoisobutyric Acid Pentapeptide", *Biochem. & Biophys. Res. Comm.*, 103(3):898-904 (1981).

Rao et al., "Molecular Structure of t-Butyloxycarbonyl-Leu-Aib-Pro-Val-Aib-Methyl Ester, a Fragment of Alamethicin and Suzukacillin: a $3_{10}$-Helical Pentapeptide", *Biopolymers*, 21:2461-2472 (1982).

Rasmussen et al., "Multiazlactones—Potential Alternatives to Isocyanate and Epoxy Resins," pp. 33-34, (1984).

Rasmussen et al., "Chemistry of Alkenylazlactones, 2 a) Reaction with thiols", *Makromol. Chem. Rapid Comm.*, 5:67-70 (1984).

Roques, Bernard P., "Peptidomimetics as Receptor Agonists or Peptidase Inhibitors: A Structural Approach in the Field of Enkephalins, ANP and CCK", *Biopolymers*, 32:407-410 (1992).

Schmitt, Heribert, "The α-Helical Conformation of the Undecapeptide Boc-L-Ala-[Aib-Ala]$_2$-Glu(OBzl)-Ala-[Aib-Ala]$_2$-OMe: Synthesis, X-Ray Crystal Structure, and Conformation in Solution", *Liebigs Ann. Chem*, pp. 1304-1321 (1982).

Schollkopf, Ulrich et al., "Asymmetric Syntheses via Heterocyclic Intermediates; VIII. Enantioselective Synthesis of (R)-α-amino Acids using L-Valine as Chiral Auxiliary Reagent," *Communications*, Dec. 1981, pp. 969-971.

Schollkopf, Ulrich, "Asymmetric Synthesis of Boc-L-Val-(R)-α-MePro-OMe, Boc-L-Val-(R)-Proome, and of Boc-L-Val-(R)-α-MePhe-OMe, Ac-L-Val-(R)-α-MePhe-OMe and Their Analogues. A New Strategy for the Synthesis of Non-Proteinogenic Dipeptides", *Liebigs Ann. Chem.*, pp. 1025-1031 (1988).

Schollkopf et al., "Asymmetrische Syntheses von α-Alkyl-α-aminocarbonsauren 2- Imidazonin-5-onen", *Angew. Chem.*, 90(2):136-138 (1978).

Schollkopf et al., "Enantioselective Synthesis of α-Methyl-a-aminocarboxylic Acids by Alkylation of the Lactim Ether of Cyclo-(L-Ala-L-Ala)", *Angew. Chem. Int. Ed. Engl.*, vol. 18(11):863-864 (1979).

Shamala et al., "The $3_{10}$ Helical Conformation of a Pentapeptide Containing a-Aminoisobutyric Acid (Aib): X-Ray Crystal Structure of Tos-(Aib)$_5$-OMe", *J.C.S. Chem. Comm.*, pp. 996-997 (1978).

Shamala et al., "The Crystal and Molecular Structure of the Amino Terminal Tetrapeptide of Alamethicin. A Novel 310 Helical Conformation", *Biochem & Biophys. Res. Comm.*, vol. 79(1):292-298, (1977).

Slagel, R.C., "Aminimides. VI. Synthesis of Aminimides from Carboxylic Acid Esters, Unsymmetrically Disubstituted Hydrazines, and Epoxides", *J. Organic Chem.*, vol. 33, No. 4 (1968).

Smith, Richard F., "Reactions of Hydrazines with Esters and Carboxylic Acids", *J. Organic Chem.—Notes*, 33(2):851-855 (1968).

Smith, G. David, "Crystal Structures and Conformational Calculations of Fragments of Alamethicin Containing Aminoisobutyric Acid," *J. Am. Chem. Soc.*, 103:1493-1501 (1981).

Taylor et al., "A convenient synthesis of 5-oxazolones. 2-phenyl-5-oxazolone", *Organic Preparations and Procedures*, 1(3):217-219 (1969).

Taylor et al., "The Synthesis of Vinyl Peptide Monomers", *Polymer Letters*, 7:597-603 (1969).

Taylor et al., "A Polymer whose Aqueous Solutions Show the Properties of Negative Thixotropy and Thermoreversible Gelation: (Poly-(Trimethylamine p-Vinylbenzimide)", *J. Polymer Science: Part C: Polymer Letters*, 24:287-289 (1986).

Taylor et al., "Synthesis of Poly(4,4-dimethyl-2-vinyl-5-oxazolone) an Interesting Material for Preparing Polymeric Agents", *Makromol Chem. Rapid Commun.*, 3:779-782 (1982).

Taylor et al., "Synthesis and Polymerization of 2-vinyl-4,4-Dimethyl-5-Oxazolone", *Polymer Letters*, 9:187-190 (1971).

Tikdari et al., "Reactions of Some 1,3-Diaminonucleophiles with Azlactones", *J. Chem. Soc. Perkin Trans. I*, 1659-1662 (1988).

Toniolo et al., "Bioorganic stereochemistry A study of the peptide oxazolones from Z-(Aib)$_n$-OH(n+2-4) in the solid state", *Int. J. Peptide Protein Res.*, 22:603-610 (1983).

Toniolo et al., "Preferred Conformations of Peptides Containing α,α-Disubstituted α-Amino Acids", *Biopolymers*, 22:205-215 (1983).

Van Roey et al., "Crystal and molecular structure of tert-butyloxycarbonyl-L-hydroxy-prolyl-α-aminoisobutyryl-α-aminoisobutryl-L-phenylalaninol", *Int. J. Peptide Protein Res.*, 19:499-505 (1982).

Van Roey et al., "tert-Butyloxycarbonyl-α-aminoisobutyryl-α-aminobutyrate Benzyl Ester, $C_{20}H_{30}N_2O_5$", *Acta Cryst.*, C39:894-896 (1983).

Venkatachalapathi et al., "X-Pro Peptides: Solution and Solid-State Conformation of Benzyloxycarbonyl-(Aib-Pro)$_2$-methyl Ester, a Type I β-Turn", *Biopolymers*, 20:1123-1136, (1961).

Delaney et al., "Sterically-Hindered Amino Acids, Directors of Peptide Conformation", in *Peptides-Synthesis-Structure-Function: Proceedings of the Seventh American Peptide Symposium*, , pp. 303-306 (Madison, Wisconsin, Jun. 14-19, 1981).

Dooley et. al., "New, Potent N-Acetylated L- and D-Amino Acid Opioid Peptides," In Peptides: Chemistry, Structure, and Biology. Proceedings of the 13th American Peptide Symposium (Hodges and Smith, Eds.), pp. 984-985 (1994).

Shikhman et.al., "Cytokeratin Peptides Mimic N-Acetyl-β-D-Glucosamine in Reactions with Antibodies and Lectins", FASEB Journal 8(4-5) (1994) and Experimental Biology 1994 Conference, Parts I and II, Anaheim, California (Apr. 24-28, 1994).

METHOD OF IDENTIFYING CHEMICAL COMPOUNDS HAVING SELECTED PROPERTIES FOR A PARTICULAR APPLICATION

RELATED APPLICATIONS

This application is a continuation of U.S. patent application Ser. No. 08/177,497, filed Jan. 5, 1994, now abandoned, the contents of which are hereby incorporated by reference in their entirety.

FIELD OF THE INVENTION

The present invention relates to a method for the modular development of aminimide- and oxazolone-derived synthetic organic molecules, posessing selected properties for a particular application. This method involves 1.) the synthesis of an array generated from modules of aminimide-forming, oxzolone, oxazolone-forming and/or oxazolone-derived molecules containing a chosen set of substituent groups which confer structural diversity and/or the reaction of these modules with other appropriate reactive groups to produce an array of molecules posessing a chosen set of diverse structural moieties; 2.) the screening of these molecules for the desired set of properties in a target application. The iterative application of this method enables molecules to be produced, having an optimum balance of properties for the particular application.

BACKGROUND OF THE INVENTION

The discovery of new molecules has traditionally focused in two broad areas, biologically active molecules, which are used as drugs for the treatment of life-threatening diseases, and new materials, which are used in commercial, and especially, in high technological applications. In both areas, the strategy used to discover new molecules has involved two basic operations: (i) a more or less random choice of a molecular candidate, prepared either via chemical synthesis or isolated from natural sources, and (ii) the testing of the molecular candidate for the property or properties of interest. This discovery cycle is repeated indefinitely until a molecule possessing the desirable property "lead molecule", is located. This "lead molecule" discovery process has been inherently ad-hoc in nature and is time-consuming, laborious, unpredictable and costly.

Once a candidate "lead" molecule has been located, the synthetic chemist must subsequently find ways to synthesize structural variants of this lead molecule to optimize its properties in the desired application. In the case where the "lead" molecule is a synthetized organic species or a natural product, the chemist is usually limited to certain structural themes and synthetic reaction schemes. These are dictated largely by the structural composition of the "lead" molecule and by the requirements of the specific application. For example, in cases where the "lead" posesses a functionally important aromatic ring, various electrophillic and nucleophillic substitutions are typically be carried out on the ring to produce variants. Each such case must be approached as a specific independent design and synthesis problem, starting each time from the beginning, because of the lack of availability of an appropriate chemistry to simply alter the structure of the lead compound to produce the variant.

Recently, some attempts have been made to modularize certain synthetic organic reaction schemes to facilitate modification and transformation of a base compound (see, for example, *Proc. Natl. Acad. Sci. USA*, 90, 6909, 1933). However, the molecules which can be produced by such attempts are extremely limited in their achievable diversity and are still bounded by factors dictated by the choice of specific structural themes. In the case where the "lead molecule" is a naturally occuring biological molecule, such as a peptide, a protein, an oligonucleotide or a carbohydrate, simple synthetic point-modifications to the lead molecule to produce variants are quite difficult to achieve.

A brief account of the strategies and tactics used in the discovery of new molecules is described below. The emphasis is on biologically interesting molecules; however, the technical problems encountered in the discovery of biologically active molecules as outlined here are also illustrative of the problems encountered in the discovery of molecules which can serve as building blocks for the development of new tools and materials for a variety of high technological applications. Furthermore, as discussed below, these problems are also illustrative of the problems encountered in the development of fabricated structures and materials for high technological applications.

Drug Design

Modern theories of biological activity state that biological activities, and therefore physiological states, are the result of molecular recognition events. For example, nucleotides can form complementary base pairs so that complementary single-stranded molecules hybridize resulting in double- or triple-helical structures that appear to be involved in regulation of gene expression. In another example, a biologically active molecule, referred to as a ligand, binds with another molecule, usually a macromolecule referred to as ligand-acceptor (e.g., a receptor or an enzyme), and this binding elicits a chain of molecular events which ultimately gives rise to a physiological state, e.g., normal cell growth and differentiation, abnormal cell growth leading to carcinogenesis, blood-pressure regulation, nerve-impulse-generation and -propagation, etc. The binding between ligand and ligand-acceptor is geometrically characteristic and extraordinarily specific, involving appropriate three-dimensional structural arrangements and chemical interactions.

A currently favored strategy for the development of agents which can be used to treat diseases involves the discovery of forms of ligands of biological receptors, enzymes, or related macromolecules, which mimic such ligands and either boost, i.e., agonize, or suppress, i.e., antagonize, the activity of the ligand. The discovery of such desirable ligand forms has traditionally been carried out either by random screening of molecules (produced through chemical synthesis or isolated from natural sources), or by using a so-called "rational" approach involving identification of a lead-structure, usually the structure of the native ligand, and optimization of its properties through numerous cycles of structural redesign and biological testing. Since most useful drugs have been discovered not through the "rational" approach but through the screening of randomly chosen compounds, a hybrid approach to drug discovery has recently emerged which is based on the use of combinatorial chemistry to construct huge libraries of randomly-built chemical structures which are screened for specific biological activities. (S. Brenner and R. A. Lerner, 1992, Proc. Natl. Acad. Sci. USA 89:53, 81)

Most lead-structures which have been used in the "rational" drug design approach are native polypeptide ligands of receptors or enzymes. The majority of polypeptide ligands, especially the small ones, are relatively unstable in physiological fluids, due to the tendency of the peptide bond to undergo facile hydrolysis in acidic media or in the presence of peptidases. Thus, such ligands are decisively inferior in a pharmacokinetic sense to nonpeptidic compounds, and are not favored as drugs. An additional limitation of small peptides as drugs is their low affinity for ligand acceptors. This phenomenon is in sharp contrast to the affinity demonstrated by large, folded polypeptides, e.g., proteins, for specific acceptors, e.g., receptors or enzymes, which can be in the subnanomolar range. For peptides to become effective drugs, they must be transformed into nonpeptidic organic structures, i.e., peptide mimetics, which bind tightly, preferably in the nanomolar range, and can withstand the chemical and biochemical rigors of coexistence with biological tissues and fluids.

Despite numerous incremental advances in the art of peptidomimetic design, no general solution to the problem of converting a polypeptide-ligand structure to a peptidomimetic has been defined. At present, "rational" peptidomimetic design is done on an ad hoc basis. Using numerous redesign-synthesis-screening cycles, peptidic ligands belonging to a certain biochemical class have been converted by groups of organic chemists and pharmacologists to specific peptidomimetics; however, in the majority of cases results in one biochemical area, e.g., peptidase inhibitor design using the enzyme substrate as a lead, cannot be transferred for use in another area, e.g., tyrosine-kinase inhibitor design using the kinase substrate as a lead.

In many cases, the peptidomimetics that result from a peptide structural lead using the "rational" approach comprise unnatural alpha-amino acids. Many of these mimetics exhibit several of the troublesome features of native peptides (which also comprise alpha-amino acids) and are, thus, not favored for use as drugs. Recently, fundamental research on the use of nonpeptidic scaffolds, such as steroidal or sugar structures, to anchor specific receptor-binding groups in fixed geometric relationships have been described (see for example Hirschmann, R. et al., 1992 *J. Am. Chem. Soc.*, 114:9699–9701; Hirschmann, R. et al., 1992 *J. Am. Chem. Soc.*, 114:9217–9218); however, the success of this approach remains to be seen.

In an attempt to accelerate the identification of lead-structures, and also the identification of useful drug candidates through screening of randomly chosen compounds, researchers have developed automated methods for the generation of large combinatorial libraries of peptides and certain types of peptide mimetics, called "peptoids", which are screened for a desirable biological activity. For example, the method of H. M. Geysen, (1984 *Proc. Natl. Acad. Sci. USA* 81:3998) employs a modification of Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. Houghton, (1985, *Proc. Natl. Acad. Sci. USA* 82:5131; and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and tested individually. Fodor et al., (1991, *Science* 251:767) described light-directed, spatially addressable parallel-peptide synthesis on a silicon wafer to generate large arrays of addressable peptides that can be directly tested for binding to biological targets. These workers have also developed recombinant DNA/genetic engineering methods for expressing huge peptide libraries on the surface of phages (Cwirla et al., 1990, *Proc. Natl. Acad. Sci. USA* 87:6378).

In another combinatorial approach, V. D. Huebner and D. V. Santi (U.S. Pat. No. 5,182,366) utilized functionalized polystyrene beads divided into portions each of which was acylated with a desired amino acid; the bead portions were mixed together, then divided into portions each of which was re-subjected to acylation with a second desirable amino acid producing dipeptides, using the techniques of solid phase peptide synthesis. By using this synthetic scheme, exponentially increasing numbers of peptides were produced in uniform which were then separately screened for a biological activity of interest.

Zuckerman et al., (1992, Int. *J. Peptide Protein Res.* 91:1) also have developed similar methods for the synthesis of peptide libraries and applied these methods to the automation of a modular synthetic chemistry for the production of libraries of N-alkyl glycine peptide derivatives, called "peptoids", which are screened for activity against a variety of biochemical targets. (See also, Symon et al., 1992, *Proc. Natl. Acad. Sci. USA* 89:9367). Encoded combinatorial chemical syntheses have been described recently (S. Brenner and R. A. Lerner, 1992, *Proc. Natl. Acad. Sci. USA* 89:5381).

The focus of these structural diversity activities on peptide synthesis chemistry is a direct result of the fact that the ability to generate structural diversity requires, as its starting point, the access to practical stepwise sequential synthesis chemistries which allow the incorporation of varied structural elements with orthogonal reactivities. To-date, these have only been worked out for the Merrifield synthesis of peptides and the Carruthers synthesis of oligonucleotides. Thus, there remains a need for an improved method for the structure-directed generation and screening of organic compounds to determine which may be suitable in a particular application.

SUMMARY OF THE INVENTION

The invention relates to a method for obtaining compounds having selected properties for a particular application by forming base modules having at least two structural diversity elements from the reaction of a first compound having at least one structural diversity element and a first reactive group, with a second compound having at least one structural diversity element and a second reactive group, wherein the first and second groups combine by an addition reaction; producing a first array of molecules by varying at least one of the structural diversity elements of the compounds when producing the base modules; and screening the array to determine a first suitable compound for the particular application.

If desired, the method can be repeated by producing a second array of molecules through the formation of base modules having structural diversity elements that are modified from those of the first suitable compound; and screening the second array of molecules to determine a second suitable compound for the particular application. The second array can be produced by forming base modules having at least two structural diversity elements in the same manner as the first array, except that the structural diversity elements are modified from those of the first suitable compound. The second array producing and screening steps can be repeated as often as necessary to achieve an optimum compound for the particular application.

Preferably, the first compound is produced by forming an oxazolone compound having at least one structural diversity element attached thereto and reacting it with a nucleophile or carbonyl compound which contains at least one structural diversity element to form a base module having one of the following structures:

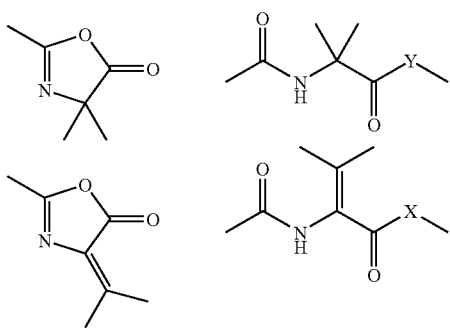

wherein at least two of the unconnected lines are connected to structural diversity elements.

Alternatively, it is also preferred to provide the first compound as an aminimide-forming compound having at least one structural diversity element attached thereto and to react it with an oxazolone or ether compound which contains at least one structural diversity element to form a base module having one of the following structures:

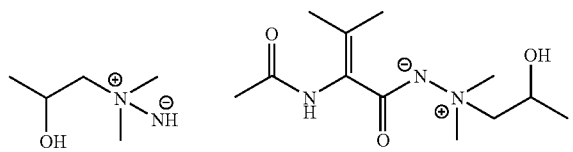

wherein at least two of the unconnected lines are connected to structural diversity elements.

Advantageously, the first and second structural diversity elements can be one of the following:
  an amino acid derivative of the form $(AA)_n$;
  a nucleotide derivative of the form $(NUCL)_n$;
  a carbohydrate derivative of the form $(CH)_n$;
  an organic moiety of an alkyl, cycloalkyl, aryl, aralkyl or alkaryl group or a substituted or heterocyclic derivative thereof, or of a naturally occurring or synthetic organic structural motif, optionally containing a reporter element, an electrophilic group, a nucleophilic group or a polymerizable group; or
  a macromolecular component.

If desired, at least one of the first and second compounds can be provided with two or more structural diversity elements, two of which can form a ring structure. The invention relates to a method for obtaining compounds having selected properties for a particular application by producing a first structurally diverse array of molecules having at least two orthogonal reactivity elements wherein a first orthogonal reactivity element is held constant for each molecule and a second orthogonal reactivity element is varied; screening the array to determine a first suitable compound for the intended application; and modifying the first suitable compound to form a second structurally diverse array of molecules. Preferably, the first suitable compound has at least two orthogonal reactivity elements, so that the method further includes modifying the first suitable compound by holding a first orthogonal reactivity element constant while varying the second orthogonal reactivity element to produce the second structurally diverse array; and screening the second structurally diverse array of molecules to determine a second suitable compound for the intended application. The method further comprises repeating the modifying and screening steps as often as necessary to achieve the optimum compound for the intended application.

The first structurally diverse array of molecules is advantageously produced by reacting either an oxazolone or aminimide compound, or combinations thereof, with first and second components which provide the orthogonal reactivity elements. It is useful for the first structurally diverse array of molecules to have one of the specific structures disclosed herein. These structures may include components such as an amino acid derivative, a nucleotide derivative, a carbohydrate derivative, an organic structural motif, a reporter element, a polymerizable organic moiety, or a macromolecular component.

This method is useful for a wide variety of applications, including the development of new biopharmaceutical agents, new monomeric species for the modular construction of separations tools, including chiral selectors, industrial detergents and additives and for the development of modular chemical intermediates for the production new materials and polymers. Specifically, the method relates to the selection of molecular modules containing appropriate structural diversity elements, the connecting of these modules together via facile high-yield addition reactions which produce discrete highly pure molecules in less than milligram quantities, in a manner such that the properties of these molecules are determined by the contributions of the individual building modules. The molecular modules of the invention may be chiral, and can be used to synthesize new compounds, structures and materials which are able to recognize biological receptors, enzymes, genetic materials, and other chiral molecules, and are thus of great interest in the fields of biopharmaceuticals, separation industrial and materials science.

BRIEF DESCRIPTION OF THE DRAWING FIGURES

FIG. 1. is a flow chart for the reaction disclosed in Example 2.

DETAILED DESCRIPTION OF THE INVENTION

The present invention is able to generate a number of different molecules for screening purposes by first forming a base module that contains at least two structural diversity elements attached thereto. These modules are formed by reacting first and second compounds, each of which has at least one structural diversity element and a reactive group. The reactive groups of the first and second compounds are such that they react with each other to form the base module by an additional reaction. By fixing one of the positions and structures of the structural diversity elements and by varying at least one of the others, an array of different molecules is easily generated. These molecules can then be screened to determine which are suitable for a particular application or target use. Once a suitable compound is identified, it can be selected for generating a further array of molecules. This is done by modifying the particular structural diversity elements that are found to be suitable, or by combining the chosen structural diversity element with an expanded or different set of second compounds or elements. This process can be repeated as often as necessary to develop the optimum compound for the particular use.

The particular base module chosen for use in accordance with the present invention is not critical and can be any one of a wide variety of structures. It has been found, however, that two particular structures which are known in the art are highly useful as such base modules, these known compounds being the oxazolones and aminamides. Thus, it is preferred to utilize compounds which are aminamide forming, oxazolone forming, oxazolone or oxazolone-derived molecules for use as the base module. Depending upon the specific structure selected, these base modules can have between two and six structural diversity elements. The specific chemistry of these molecules, as well as an identification of the structural diversity elements and reactivity groups, follows.

Oxazolones

Oxazolones, or azlactones, are structures of the general formula:

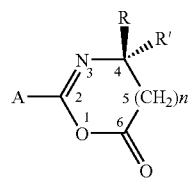

where A, R, and R' are functional groups and n is 0–3.

Oxazolones may posess two substituents at the 4-position. When these substituents are not equivalent, the carbon atom at the 4-position is asymmetric and two non-superimposable oxazolone structures (azlactones) result:

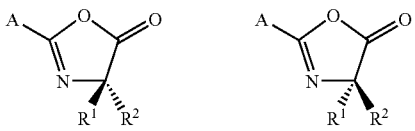

Chiral oxazolones possessing a single 4-position non hydrogen substituent (also known as 5(4H)-oxazolones), derived from (chiral) natural amino acid derivatives, including activated acylamino acyl structures, have been prepared and isolated in the pure, crystalline state (Bodansky, M.; Klausner, Y. S.; Ondetti, M. A. in "Peptide Synthesis", Second Edition, John Wiley & Sons, New York, 1976, p. 14 and references cited therein). The facile, base-catalyzed racemization of several of these oxazolones has been studied in connection with investigations of the serious racemization problem confronting peptide synthesis (see Kemp, D. S. in "The Peptides, Analysis, Synthesis, and Biology", Vol. 1, Gross, E. & Meienhofer, J. editors, 1979, p. 315).

Racemization during peptide synthesis becomes very extensive when the desired peptide is produced by aminolysis of activated peptidyl carboxyl, as in the case of peptide chain extension from the amino terminus, e.g. I–VI shown below (see Atherton, E.; Sheppard, R. C. "Solid Phase Peptide Synthesis, A Practical Approach", IRL Press at Oxford University Press, 1989, pages 11 and 12). An extensively studied mechanism describing this racemization involves conversion of the activated acyl derivative (II) to an oxazolone (III) followed by facile base-catalyzed racemization of the oxazolone via a resonance-stabilized intermediate (IV) and aminolysis of the racemic oxazolone (V) producing racemic peptide products (VI).

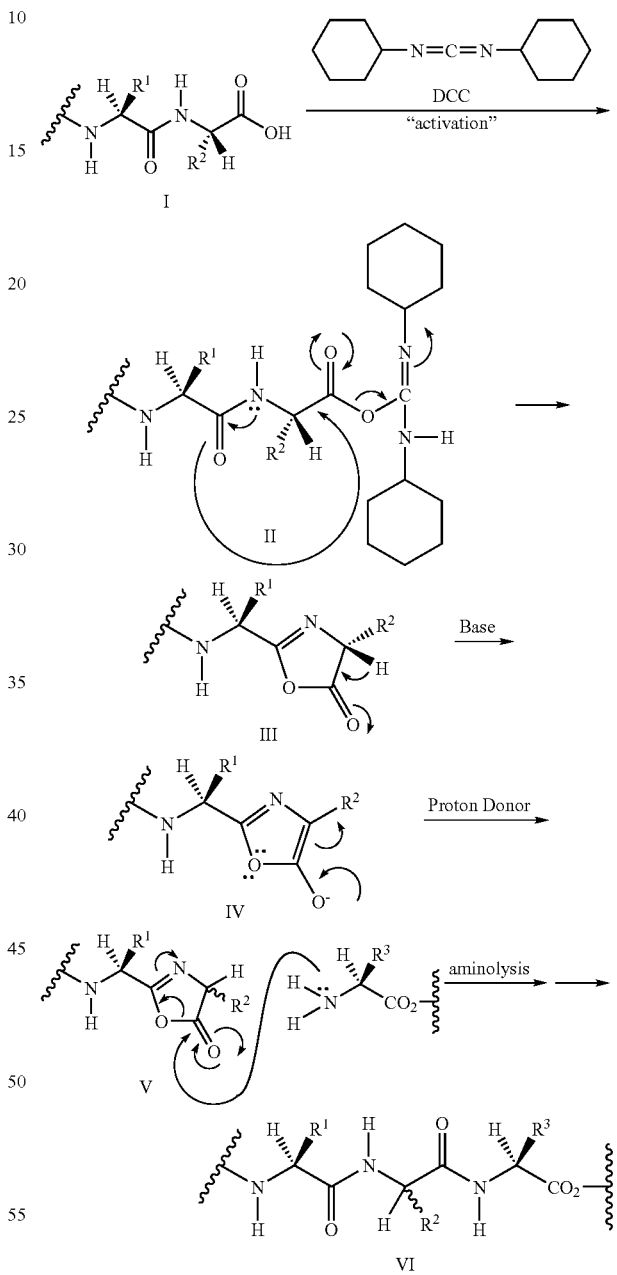

Extensive research on the trapping of oxazolones III (or of their activated acyl precursors II) to give acylating agents which undergo little or no racemization upon aminolysis has been carried out, and successes in this area (such as the use of N-hydroxybenzotriazole) have greatly advanced the art of peptide synthesis (Kemp, D. S. in "The Peptides, Analysis, Synthesis, and Biology", Vol. 1, Gross, E. & Meienhofer, J. editors, 1979, p. 315).

Thus, attempts to deal with the racemization problem in peptide synthesis have involved suppressing or avoiding the formation of oxazolone intermediates altogether.

Oxazolones having at least one hydrogen substituent at the 4-position can also undergo a variety of rearrangements and side-reactions (cf., 23 *Tetrahedron* 3363 (1967)), which may interfere with other desired transformations. This is illustrated for the case of the oxazolone formed from the cyclization of N-acryloyl glycine:

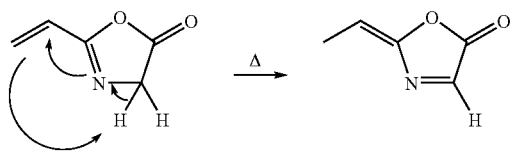

Oxazolones containing two non-hydrogen substituents at the four position are structurally precluded from undergoing these racemizations and side-reactions. These disubstituted oxazolones may be obtained chirally pure and may be subjected to the transformations which are the subject of this invention with retention of the chirality at this position.

When the substituent at the 2-position is capable of undergoing addition reactions, these may be carried out with retention of the chirality at the 4-position to produce new oxazolones. This is shown for the Michael-type addition to an alkenyl oxazolone as follows:

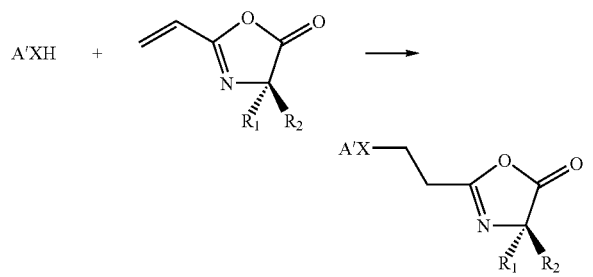

where X=S or NR and A' is a structural diversity group.

Synthesis of Oxazolones

Oxazolones may be prepared from the appropriate amino acid using any of a number of standard acylation and cyclization techniques well-known to those skilled in the art, e.g.:

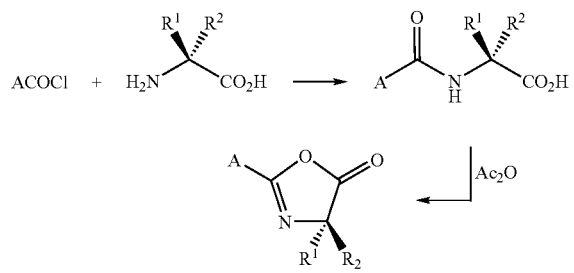

These oxazolones may be isolated in the pure state or may be generated in-situ from the acyl amino acid by treatment, for example, with equivalent amounts of triethyl amine and ethyl chloroformate in benzene. Following the evolution of carbon monoxide and the removal of the triethyl ammonium chloride formed by filtration. the solution of the oxazolone may be utilized directly for subsequent transformations.

Reactions of Oxazolones

Ring-opening Addition

Oxazolones may be subjected to ring opening reactions with a variety of nucleophiles, as shown below:

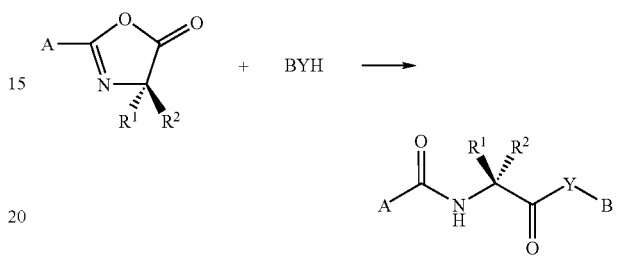

In the structure above, Y represents an oxygen, sulfur, or nitrogen atom. $R^1$ and $R^2$ differ from one another and taken alone each signifies one of the following: alkyl including carbocyclic and substituted forms thereof; aryl, aralkyl, alkaryl, and substituted or heterocyclic versions thereof.

The above ring-opening reaction can be carried out either in an organic solvent such as methylene chloride, ethyl acetate, dimethyl formamide (DMF) or in water at room or higher temperatures, in the presence or absence of acids, such as carboxylic, other proton or Lewis-acids, or bases, such as tertiary amines or hydroxides, serving as catalysts.

This reaction may be used to generate an array of adducts, posessing combinations of the structural diversity elements A and C, as shown:

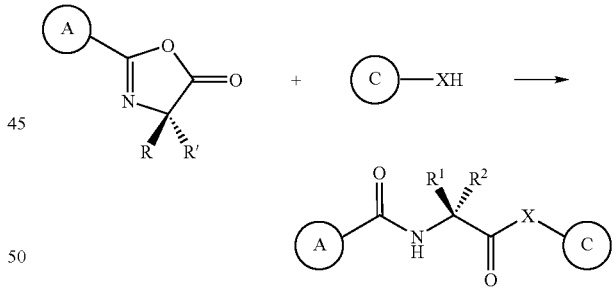

In addition, by appropriate selection of the R and R' groups, two additional diversity elements can be provided in those positions. Thus, the compound shown can have from two to four structural diversity elements attached to the base module as desired.

Carbonyl Addition

When both substituents in the 4-position are hydrogen, i.e., the oxazolone is formed from cyclization of an acyl glycine, the ring may undergo a high yield condensation addition reaction with aldehyde or ketone-containing structural groups at the 4-position. This reaction may be used to generate an array of adducts, posessing combinations of the structural diversity elements A and B, as shown:

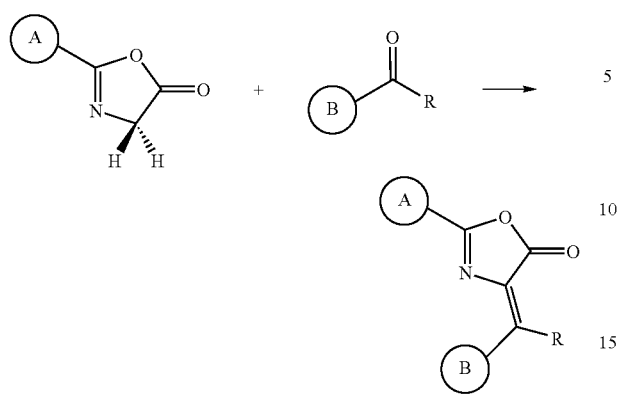

Again, as noted above, the R group can be selected to be a diversity element to provide an additional structural diversity group on the oxazolone molecule.

Combination of the Two Reactions

The resulting adduct may subsequently undergo a high yield ring-opening addition reactrion with a wide variety of SH, NH and OH containing nucleophiles. This reaction sequence may, thus, be used to generate an array of adducts, posessing combinations of the structural diversity elements A, B and C, as shown

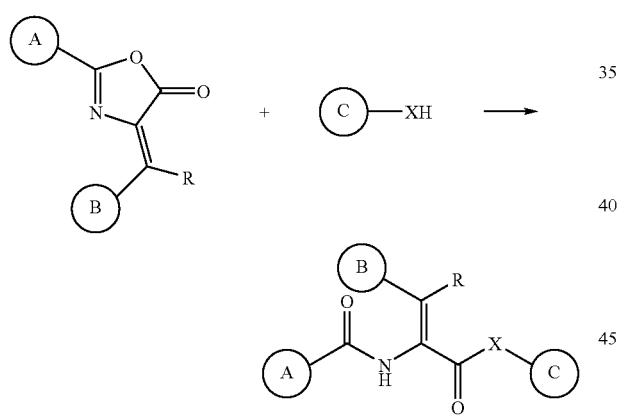

Again, as noted above, the R group can be selected to be a diversity element to provide an additional structural diversity group on the oxazolone molecule.

This is illustrated for the case of the in-situ generation of the oxazolone from hippuric acid, followed by removal of the triethylammonium chloride by filtration, the addition of benzaldehyde to form the unsaturated adduct and the ring opening addition of benzylamine to give the tris-phenyl substituted adduct shown:

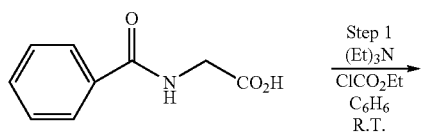

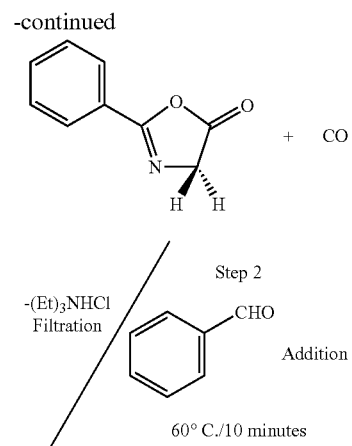

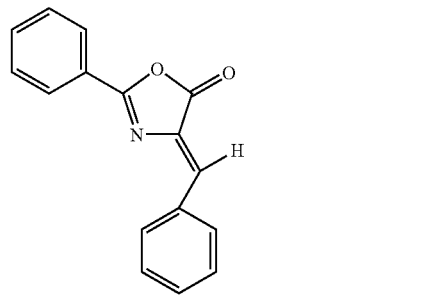

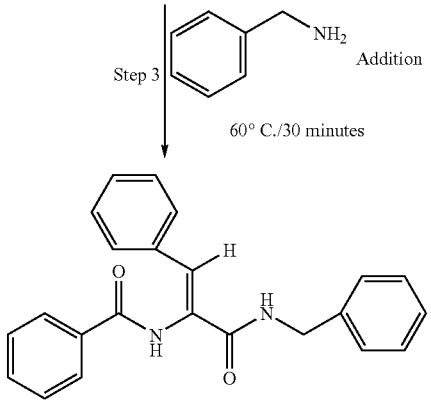

The ability of these various reactions to be carried out in a stepwise sequential manner using modules chosen in a structure-directed manner allows the production of structurally directed thematic diversity libraries, having structural elements systematically varied around a basic motif.

Aminimides

Aminimides are zwitterionic structures described by the resonance hybrid of the two energetically comparable Lewis structures shown below:

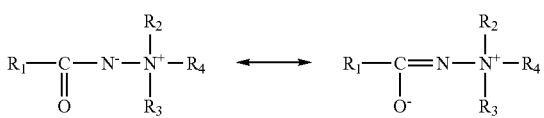

The tetrasubstituted nitrogen of the aminimide group can be asymmetric rendering aminimides chiral as shown by the two enantiomers below:

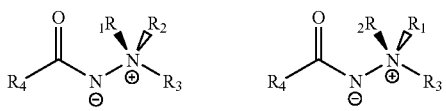

As a result of the polarity of their structures, but lack of net charge, simple aminimides are freely soluble in both water and (especially) organic solvents.

Dilute aqueous solutions of aminimides are neutral and of very low conductivity; the conjugate acids of simple aminimides are weakly acidic, pKa of ca. 4.5. A striking property of aminimides is their hydrolytic stability, under acidic, basic, or enzymatic conditions. For example, boiling trimethyl amine benzamide in 6 N NaOH for 24 hrs leaves the aminimide unchanged. Upon thermolytic treatment, at temperatures exceeding 180° C., aminimides decompose to give isocyanates as follows.

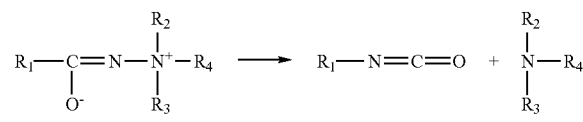

Synthetic Routes to Aminimides

Aminimides can be synthesized in a variety of different ways. The compounds of the present invention can be synthesized by many routes. It is well known in the art of organic synthesis that many different synthetic protocols can be used to prepare a given compound. Different routes can involve more or less expensive reagents, easier or more difficult separation or purification procedures, straightforward or cumbersome scale-up, and higher or lower yield. The skilled synthetic organic chemist knows well how to balance the competing characteristics of competing strategies. Thus, the compounds of the present invention are not limited by the choice of synthetic strategy and any synthetic strategy that yields the compounds described above can be used.

Aminimides via Alkylation of N,N-Disubstituted Hydrazides

Alkylation of a hydrazide followed by neutralization with a base produces an aminimide

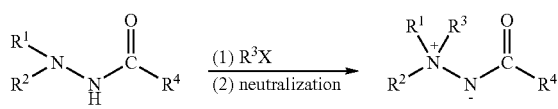

This alkylation is carried out in a suitable solvent, such as a hydroxylic solvent, e.g., water, ethanol, isopropanol or a dipolar aprotic solvent, e.g., DMF, DMSO, acetonitrile, usually with heating. An example of this reaction is the synthesis of the trifluoroacyl-analide dipeptide elastase inhibitor mimetics shown in the examples below.

Aminimides via Acylation of 1,1,1-Trialkyl Hydrazinium Salts

Acylation of a suitable trialkyl hydrazinium salt by an acyl derivative or isocyanate in the presence of a strong base in a suitable organic solvent, e.g. dioxane, ether, acetonitrile, etc. produces good yields of aminimides.

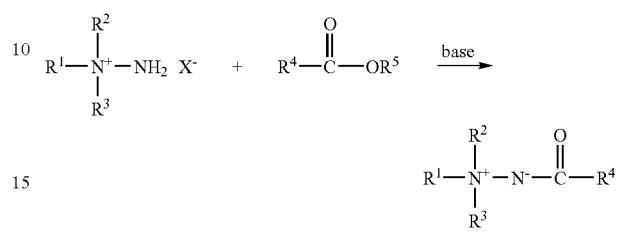

Aminimides via the Hydrazine-Epoxide-Ester Reaction

A very useful and versatile synthesis of aminimides involves the one-pot reaction of an epoxide, an asymetrically disubstituted hydrazine, and an ester in a hydroxylic solvent, usually water or an alcohol, which is allowed to proceed usually at room temperature over several hours to several days.

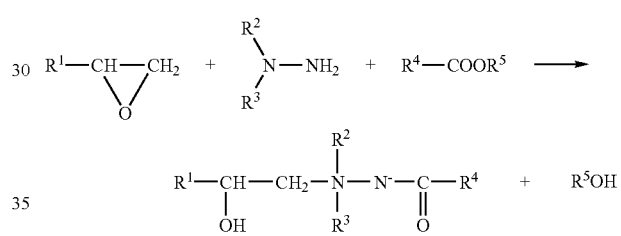

In the equation above, R1, R2 and R3 are selected from a set of diverse structural types (e.g. alkyl, carbocyclic, aryl, aralkyl, alkaryl or many substituted versions thereof), and R4 and R5 are alkyl, carbocyclic, cycloalkyl, aryl or alkaryl.

The rates for the above reaction increase with increasing electrophilicity of the ester component. Generally, a mixture of 0.1 mol of each of the reactants in 50–100 ml of an appropriate solvent is stirred for the required period at room temperature (the reaction may be monitored by thin layer chromatography). At the end of this period, the solvent is removed in vacuo to give the crude product.

Any of the various R groups illustrated in all of these aminimide and aminimide-forming structures may be selected to be structural diversity elements.

The ability of these various reactions to be carried out using modules chosen in a structure-directed manner allows the production of structurally directed thematic diversity libraries, having structural elements systematically varied around a basic motif.

Further details on the reaction possibilities for the oxazolone and aminimide compounds can be found in two PCT applications PCT/US93/12591 and PCT/US93/12612, each filed on Dec. 28, 1993, and entitled Modular Design And Synthesis of Oxazolone-Derived Molecules and Modular Design And Synthesis Of Aminimide-Derived Molecules, respectively. The content of each of those applications is expressly incorporated herein by reference thereto to the extent necessary to understand the metes and bounds of this invention.

Mixed Aminimide-Oxazolones

A particularly useful embodiment of the invention is the synthesis of mixed aminimide-oxazolone molecules, as shown below. This scenario allows the incorporation of multiple structural diversity elements as shown:

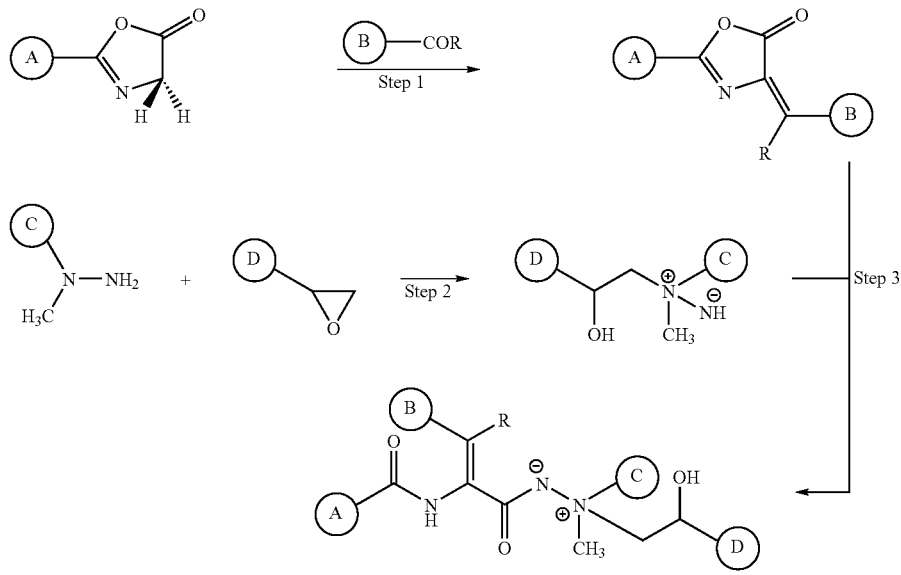

30

Again, as noted above, the R and methyl groups can be replaced with additional structural diversity elements so that a total of six can be provided on the mixed aminamide-oxazolone base module.

Structural Diversity Elements

Any of a wide variety of structural diversity elements can be used. These elements would include:

1) Amino acid derivatives of the form (AA)N, which would include, for example, natural and synthetic amino acid residues (N=1) including all of the naturally occuring alpha amino acids, especially alanine, arginine, asparagnine, aspartic acid, cysteine, glutamine, glutamic acid, glycine, histidine, isoleucine, leucine, lysine, methionine, phenylalanine, proline, serine, threonine, tryptophan, tyrosine; the naturally occuring disubstituted amino acids, such as amino isobutyric acid, and isovaline, etc.; a variety of synthetic amino acid residues, including alpha-disubstituted variants, species with olefinic substitution at the alpha position, species having derivatives, variants or mimetics of the naturally occuring side chains; N-Substituted glycine residues; natural and synthetic species known to functionally mimic amino acid residues, such as statine, bestatin, etc. Peptides (N=2–30) constructed from the amino acids listed above, such as angiotensinogen and its family of physiologically important angiotensin hydrolysis products, as well as derivatives, variants and mimetics made from various combinations and permutations of all the natural and synthetic residues listed above. Polypeptides (N=31–70), such as big endothelin, pancreastatin, human growth hormone releasing factor and human pancreatic polypeptide. Proteins (N>70) including structural proteins such as collagen, functional proteins such as hemoglobin, regulatory proteins such as the dopamine and thiombin receptors.

2) Nucleotide derivatives of the form (NUCL)N, which includes natural and synthetic nucleotides (N=1) such as adenosine, thymine, guanidine, uridine, cystosine, derivatives of these and a variety of variants and mimetics of the purine ring, the sugar ring, the phosphate linkage and combinations of some or all of these. Nucleotide probes (N=2–25) and oligonucleotides (N>25) including all of the various possible homo and heterosynthetic combinations and permutations of the naturally occuring nucleotides, derivatives and variants containing synthetic purine or pyrimidine species or mimics of these, various sugar ring mimetics, and a wide variety of alternate backbone analogues including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogues.

3) Carbohydrate derivatives of the form (CH)n. This would include natural physiologically active carbohydrates such as including related compounds such as glucose, galactose, sialic acids, beta-D-glucosylamine and nojorimycin which are both inhibitors of glucosidase, pseudo sugars, such as 5a-carba-2-D-galactopyranose, which is known to inhibit the growth of Klebsiella pneumonia (n=1), synthetic carbohydrate residues and derivatives of these (n=1) and all of the complex oligomeric permutations of these as found in nature, including high mannose oligosaccharides, the known antibiotic streptomycin (n>1).

4) A naturally occurring or synthetic organic structural motif. This term is defined as meaning an organic molecule having a specific structure that has biological activity, such as having a complementary structure to an enzyme, for instance. This term includes any of the well known base structures of pharmaceutical compounds including pharmacophores or metabolites thereof. These include beta-lactams, such as pennicillin, known to inhibit bacterial cell wall biosynthesis; dibenzazepines, known to bind to CNS receptors, used as antidepressants; polyketide macrolides, known to bind to bacterial ribosymes, etc. These structural motifs are generally known to have specific desirable binding properties to ligand acceptors.

5) A reporter element such as a natural or synthetic dye or a residue capable of photographic amplification which possesses reactive groups which may be synthetically incorporated into the oxazolone structure or reaction scheme and may be attached through the groups without adversely interfering with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) An organic moiety containing a polymerizable group such as a double bond or other functionalities capable of undergoing condensation polymerization or copolymerization. Suitable groups include vinyl groups, oxirane groups, carboxylic acids, acid chlorides, esters, amides, lactones and lactams. Other organic moiety such as those defined for R and R' may also be used.

7) A macromolecular component, such as a macromolecular surface or structures which may be attached to the oxazolone modules via the various reactive groups outlined above in a manner where the binding of the attached species to a ligand-receptor molecule is not adversely affected and the interactive activity of the attached functionality is determined or limited by the macromolecule. This includes porous and non-porous inorganic macromolecular components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrene-divinyl benzene beads, various methacrylate beads, PVA beads, and the like, commonly used for protein purification, water softening and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range from about 1000 Daltons to as high as possible. They may take the form of nanoparticles (dp=100–1000 Angstroms), latex particles (dp=1000–5000 Angstroms), porous or non-porous beads (dp=0.5–1000 microns), membranes, gels, macroscopic surfaces or functionalized or coated versions or composites of these.

8) A structural moiety selected from the group including cyano, nitro, halogen, oxygen, hydroxy, alkoxy, thio, straight or branched chain alkyl, carbocyclic aryl and substituted or heterocyclic derivatives thereof, wherein R and R' may be different in adjacent n units and have a selected stereochemical arrangement about the carbon atom to which they are attached;

As used herein, the phrase linear chain or branched chained alkyl groups means any substituted or unsubstituted acyclic carbon-containing compounds, including alkanes, alkenes and alkynes. Alkyl groups having up to 30 carbon atoms are preferred. Examples of alkyl groups include lower alkyl, for example, methyl, ethyl, n-propyl, iso-propyl, n-butyl, iso-butyl or tert-butyl; upper alkyl, for example, cotyl, nonyl, decyl, and the like; lower alkylene, for example, ethylene, propylene, propyldiene, butylene, butyldiene; upper alkenyl such as 1-decene, 1-nonene, 2,6-dimethyl-5-octenyl, 6-ethyl-5-octenyl or heptenyl, and the like; alkynyl such as 1-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few. Specific substituted alkyl groups can be, for example, alkoxy such as methoxy, ethoxy, butoxy, pentoxy and the like, polyhydroxy such as 1,2-dihydroxypropyl, 1,4-dihydroxy-1-butyl, and the like; methylamino, ethylamino, dimethylamino, diethylamino, triethylamino, cyclopentylamino, benzylamino, dibenzylamino, and the like; propanoic, butanoic or pentanoic acid groups, and the like; formamido, acetamido, butanamido, and the like, methoxycarbonyl, ethoxycarbonyl or the like, chloroformyl, bromoformyl, 1,1-chloroethyl, bromo ethyl, and the like, or dimethyl or diethyl ether groups or the like.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like. such cyclic groups may also contain various substituents in which one or more hydrogen atoms has been replaced by a functional group. Such functional groups include those described above, and lower alkyl groups as described above. The cyclic groups of the invention may further comprise a heteroatom. For example, in a specific embodiment, $R_2$ is cycohexanol.

As used herein, substituted and unsubstituted aryl groups means a hydrocarbon ring bearing a system of conjugated double bonds, usually comprising an even number of 6 or more (pi) electrons. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocylic groups, functional groups on the aryl groups can be nitro groups.

As mentioned above, these structural moieties can also be any combination of alkyl, carbocyclic or aryl groups, for example, 1-cyclohexylpropyl, benzylcyclohexylmethyl, 2-cyclohexyl-propyl, 2,2-methylcyclohexylpropyl, 2,2methylphenylpropyl, 2,2-methylphenylbutyl, and the like.

Orthogonal Reactivities

A key element of the present method is the presence of at least two compounds, each having a reactive group capable of forming an addition compound with the other and carrying at least one of the structural diversity groups. These compounds are used to form the aminimide and the oxazolone base modules. These compounds may take the form of either A.) multiple reactive groups which are capable of being "turned on" independently of each other or B.) groups with multiple states with differing reactivities which may be addressed or brought into being at different times or under different conditions in a reaction sequence. It is highly desirable, although not absolutely necessary, that each individual reaction be a high-yielding addition reaction without possible interfering side-reactions so that isolation and purification steps are not necesary, or, at least, are held to a minimum.

Specifically preferred reactive groups to generate the aminimide and oxazolone structures and the resulting base modules are listed below in tables 1, 2 and 3. The bonds in the structures in these figures represent potential points of attachment for the attachment of the structural diversity elements to the first and second compounds and to the base modules.

TABLE 1
Oxazolone Modules

| Reactivity Groups | Base Modules |
| --- | --- |
| [oxazolone structure]; HY— (Y = N, S, O) | [acetamido base module with Y linkage] |
| [oxazolone structure]; C=O | [isopropylidene oxazolone] |
| [isopropylidene oxazolone]; HY— (Y = N, S, O) | [acetamido alkene with Y linkage] |
| $NH_2$–C(CH$_3$)$_2$–$CO_2H$; —CO2H/Cl (ClCO2Et/Et3N) | [oxazolone] |
| [Z-substituted oxazolone]; HX— (X = S—, N〈 ); (Z = $CH_2$=CH—, etc.) | [X-Z substituted oxazolone] |

— Represents potential points of attachment for structural diversity elements

TABLE 2 / TABLE 2-continued
Aminimide Modules

| Reactivity Groups | Base Modules |
| --- | --- |
| —COOH ; H2NN〈 | —CONHN〈 |
| —NCO ; H2NN〈 | —NHCONHN〈 |
| —OCOCl ; H2NN〈 | —OCONHN〈 |
| —SCOCl ; H2NN〈 | —SCONHN〈 |
| —CONHN〈 —X (neutr.) | —CONN$^{\ominus}$|$^{\oplus}$— |
| —CONHN〈 [epoxide] | —CONN$^{\ominus}$|$^{\oplus}$—CH$_2$CH(OH)CH$_3$ |
| —NHCONHN〈 —X (neutr.) | —NHCONN$^{\ominus}$|$^{\oplus}$— |
| —NHCONHN〈 [epoxide] | —NHCONN$^{\ominus}$|$^{\oplus}$—CH$_2$CH(OH)CH$_3$ |
| —OCONHN〈 —X (neutr.) | —OCONN$^{\ominus}$|$^{\oplus}$— |
| —OCONHN〈 [epoxide] | —OCONN$^{\ominus}$|$^{\oplus}$—CH$_2$CH(OH)CH$_3$ |
| —SCONHN〈 —X (neutr.) | —SCONN$^{\ominus}$|$^{\oplus}$— |

TABLE 2-continued

Aminimide Modules

| Reactivity Groups | Base Modules |
| --- | --- |
| (structures) | (structures) |
| (structures) | (structures) |
| (structures) | (structures) |

TABLE 2-continued

Aminimide Modules

| Reactivity Groups | Base Modules |
| --- | --- |
| (structures) | (structures) |
| (structures) | (structures) |

— Represents potential points of attachment for structural diversity elements

TABLE 3

Aminimide-Oxazolone Modules

| Reactivity Groups | Base Modules |
| --- | --- |
| (structures) | (structures) |
| (structures) | (structures) |

— Represents potential points of attachment for structural diversity elements

TABLE 2-continued

Aminimide Modules

| Reactivity Groups | Base Modules |
| --- | --- |
| (structures) | (structures) |
| (structures) | (structures) |
| (structures) | (structures) |

EXAMPLE 1.

This example describes the generation of a matrix of 16 molecules around the following aryl-heterocycle-alicyclic amine structural theme.

Theme:

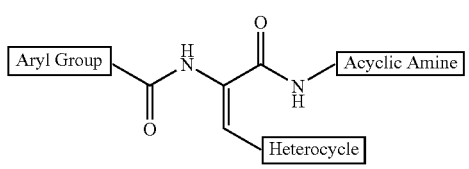

The 2-phenyl and 2-(2-naphthyl)-5-oxazolones (produced by reacting the lithium salt of glucine with the aryl acid chlorides, followed by cyclization with ethyl chloroformate at 0 C) were reacted with 2-furfural, 3-fufural, 2-thiophenal and 3-thiophenyl to produce the oxazolones functionalized at the 4-position. This was followed by subsequent ring-opening addition of 4-(3-aminopropylmorpholine and 1-(3-aminopropyl)-2-pipicoline to form the adducts shown. The reactions were carried out in individual vials such that each vial contained one pure final compound as follows:

1.) equimolar quantities of the oxazolone and the aldehyde dissolved in dry benzene (25 ml/gm reactants) were heated to 75 C for 15 minutes; 2.) the reaction mixture was cooled to 10 C and the amine was added dropwise with stirring; 3.) the mixture was re-heated to 75 C for 20 minutes and 4.) the solvent was removed in vacuo to give the crude solid product.

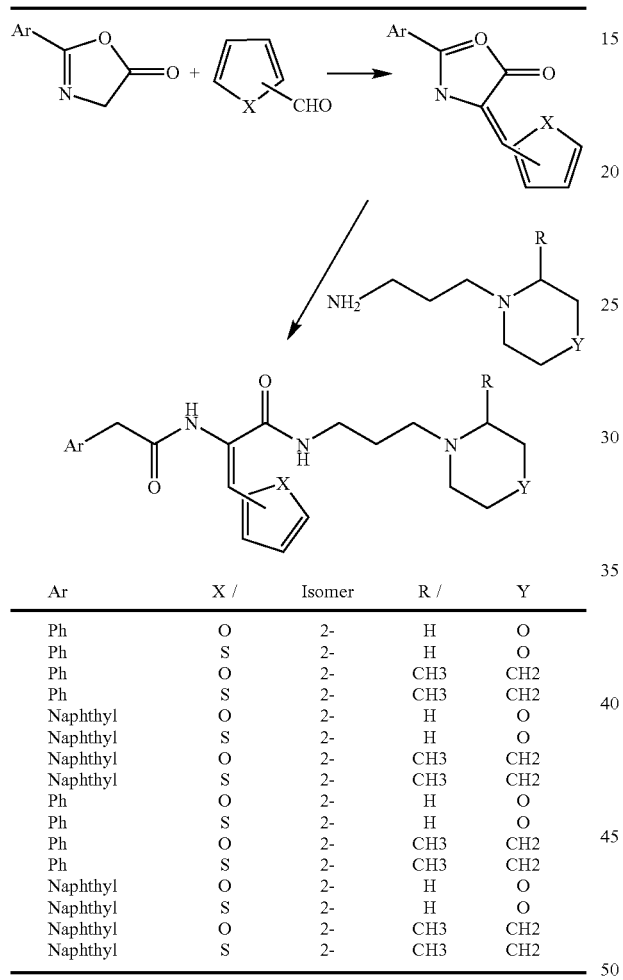

| Ar | X / | Isomer | R / | Y |
|---|---|---|---|---|
| Ph | O | 2- | H | O |
| Ph | S | 2- | H | O |
| Ph | O | 2- | CH3 | CH2 |
| Ph | S | 2- | CH3 | CH2 |
| Naphthyl | O | 2- | H | O |
| Naphthyl | S | 2- | H | O |
| Naphthyl | O | 2- | CH3 | CH2 |
| Naphthyl | S | 2- | CH3 | CH2 |
| Ph | O | 2- | H | O |
| Ph | S | 2- | H | O |
| Ph | O | 2- | CH3 | CH2 |
| Ph | S | 2- | CH3 | CH2 |
| Naphthyl | O | 2- | H | O |
| Naphthyl | S | 2- | H | O |
| Naphthyl | O | 2- | CH3 | CH2 |
| Naphthyl | S | 2- | CH3 | CH2 |

EXAMPLE 2.

The following example outlines the generation of a matrix of 16 molecules around the basic structural theme of a hydroxy-proline transition state mimetic inhibitor for proteases:

Structural Theme:

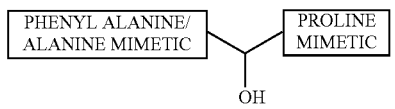

This mimetic was synthesized by reacting styrene oxide or propylene oxide, ethyl acetate or methyl benzoate with four commercially available cyclic hydrazines (as mimetics of proline) in isopropanol in 16 individual sample vials, as shown in FIG. 1.

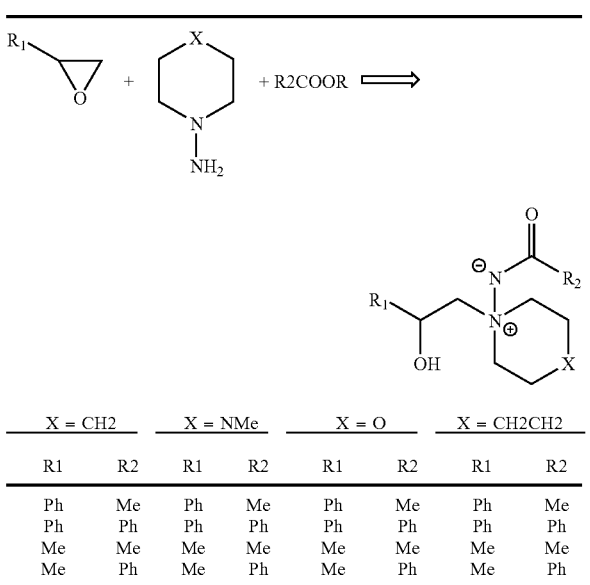

| X = CH2 | | X = NMe | | X = O | | X = CH2CH2 | |
|---|---|---|---|---|---|---|---|
| R1 | R2 | R1 | R2 | R1 | R2 | R1 | R2 |
| Ph | Me | Ph | Me | Ph | Me | Ph | Me |
| Ph | Ph | Ph | Ph | Ph | Ph | Ph | Ph |
| Me | Me | Me | Me | Me | Me | Me | Me |
| Me | Ph | Me | Ph | Me | Ph | Me | Ph |

These 16 materials were isolated in essentially quantitative yield on removal of the reaction solvent by evaporation and purified samples were obtained as crystalline solids after recrystallization from ethyl acetate and characterized by $^1$H-NMR, FTIR and other analytical techniques. The set of molecules where X=CH2 was tested as competitive inhibitiors of the enzyme chymotrypsin in a standard assay using a BTEE substrate. The results found for Ki were 200 uM for R1=Ph, R2=Me; 130 uM for R1=Me, R2=Ph; 500 uM for R1=Ph, R2=Ph; and R1=Me, R2=Me was found to not be an inhibitor. These results indicate a preference of the enzyme in this assay for one phenyl and one methyl, with the phenyl being preferred in the R1 position. Based on these results, a second array was synthesized using phenyl groups in this position having a variety of different substituent groups for further testing against the enzyme.

What is claimed is:

1. A method of identifying a molecule having selected properties for a particular application which comprises the steps of:
   a) forming a base module having at least two structural diversity elements by reacting a first compound having at least one structural diversity element and a first reactive group with a second compound having at least one structural diversity element and a second reactive group which is different from said first reactive group, wherein the first and second reactive groups combine by a solution phase addition reaction;
   b) producing a first array of at least two different base modules by repeating step a) at least one time while varying at least one of the structural diversity elements of the first or second compounds to produce at least one additional base module having at least two structural diversity elements, at least one of which differs from the structural diversity elements of the base module produced in step a); and c) simultaneously screening the first array of base modules in accordance with a standard determined by said particular application to identify a first suitable compound for the particular application.

2. The method of claim 1 which further comprises producing a second array by forming additional base modules having structural diversity elements that are modified from those of the first suitable molecule; and simultaneously screening the second array to determine a second suitable molecule for the particular application.

3. The method of claim 2 wherein the second array is produced by forming a base module having at least two structural diversity elements by reacting a first compound having at least one structural diversity element and a first reactive group, with a second compound having at least one structural diversity element and a second reactive group, wherein the first and second groups combine by a solution phase addition reaction, and wherein the structural diversity elements are modified from those of the first suitable molecule.

4. The method of claim 3 which further comprises repeating the second array producing and screening steps.

5. The method of claim 1 wherein the first compound is an oxazolone compound having at least one structural diversity element attached thereto.

6. The method of claim 5 wherein the second compound is a nucleophile or carbonyl compound which is capable of reaction with the oxazolone and which contains at least one structural diversity element.

7. The method of claim 1 wherein the first compound is an aminimide-forming compound having at least one structural diversity element attached thereto.

8. The method of claim 7 which wherein the second compound is an ether compound which is capable of reaction with the aminimide-forming compound and which contains at least one structural diversity element.

9. The method of claim 1 which further comprises the selecting wherein each of the first and second structural diversity elements is one of the following:

an amino acid derivative;

a nucleotide derivative;

a carbohydrate derivative;

an organic moiety of an alkyl, cycloakyl, aryl, aralkyl or alkaryl group or a substituted or heterocyclic derivative thereof, or of a naturally occurring or synthetic organic structural motif, optionally containing a reporter element, an electrophilic group, a nucleophilic group or a polymerizable group; or a macromolecular component.

10. The method of claim 1, which further comprises providing at least one of the first and second compounds with at least two structural diversity elements.

11. The method of claim 1 which further comprises providing each of the first and second compounds with at least two structural diversity elements.

12. The method of claim 10 wherein the at least two structural diversity elements of the first compound form a ring structure.

13. The method of claim 11 wherein the at least two structural diversity elements of the first or second compound form a ring structure.

* * * * *

UNITED STATES PATENT AND TRADEMARK OFFICE
CERTIFICATE OF CORRECTION

PATENT NO. : 7,034,110 B2 Page 1 of 1
APPLICATION NO. : 10/764112
DATED : April 25, 2006
INVENTOR(S) : Joseph C. Hogan, Jr.

It is certified that error appears in the above-identified patent and that said Letters Patent is hereby corrected as shown below:

Col. 10, lines 47-52, replace

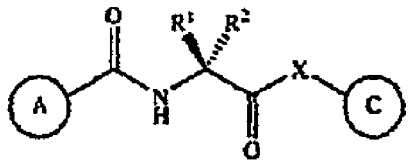

with

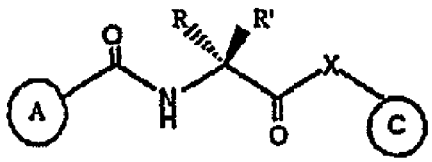

Signed and Sealed this

Sixteenth Day of January, 2007

JON W. DUDAS
*Director of the United States Patent and Trademark Office*